(12) United States Patent
Wang

(10) Patent No.: US 8,673,294 B2
(45) Date of Patent: Mar. 18, 2014

(54) IMMUNOISOLATION PATCH SYSTEM FOR CELLULAR TRANSPLANTATION

(75) Inventor: Taylor G. Wang, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 268 days.

(21) Appl. No.: 12/989,490

(22) PCT Filed: Apr. 23, 2009

(86) PCT No.: PCT/US2009/041515
§ 371 (c)(1),
(2), (4) Date: Jan. 10, 2011

(87) PCT Pub. No.: WO2009/132173
PCT Pub. Date: Oct. 29, 2009

(65) Prior Publication Data
US 2011/0092949 A1    Apr. 21, 2011

Related U.S. Application Data

(60) Provisional application No. 61/047,860, filed on Apr. 25, 2008.

(51) Int. Cl.
*A61K 35/12* (2006.01)
*A61K 9/00* (2006.01)
*A61K 9/50* (2006.01)

(52) U.S. Cl.
USPC .......... 424/93.7; 424/484; 424/486; 424/488; 435/177; 435/179; 435/180; 435/182

(58) Field of Classification Search
None
See application file for complete search history.

(56) References Cited

U.S. PATENT DOCUMENTS

| 5,545,423 | A | | 8/1996 | Soon-Shiong et al. | |
|---|---|---|---|---|---|
| 5,578,314 | A | | 11/1996 | Cochrum et al. | |
| 5,879,709 | A | * | 3/1999 | Soon-Shiong et al. | 424/484 |
| 5,997,900 | A | * | 12/1999 | Wang et al. | 424/451 |
| 6,365,385 | B1 | * | 4/2002 | Opara | 435/178 |
| 2001/0049130 | A1 | | 12/2001 | Spielberg | |
| 2007/0237749 | A1 | | 10/2007 | Wang | |

FOREIGN PATENT DOCUMENTS

WO  96/28029 A1  9/1996
WO  2007/126993 A2  11/2007

OTHER PUBLICATIONS

Schneider et al, Biomaterials, 2002, vol. 22, issue 14, pp. 1961-1970.*
Peter Kopp, "Perspective: Genetic Defects in the Etiology of Congenital Hypothyroidism", Endocrinology, Jun. 2002, vol. 143, pp. 2019-2024.
International Search Report, International Application No. PCT/US2009/041515 filed Apr. 23, 2009.

* cited by examiner

*Primary Examiner* — Allison Ford
(74) *Attorney, Agent, or Firm* — Jeffrey N. Townes; LeClairRyan

(57) ABSTRACT

An immunoisolation patch system, and particularly a patch system comprising multiple immunoisolation microcapsules, each encapsulating biological material such as cells for transplantation, which can be used in the prophylactic and therapeutic treatment of disease in large animals and humans without the need for immunosuppression.

22 Claims, 12 Drawing Sheets

IMMUNOISOLATION PATCH SYSTEM FOR CELLULAR TRANSPLANTATION

CROSS REFERENCE TO RELATED APPLICATIONS

The present invention claims priority to U.S. Provisional Patent Application No. 61/047,860, filed Apr. 25, 2008, which is incorporated herein by reference in its entirety.

STATEMENT REGARDING FEDERALLY-SPONSORED RESEARCH

This invention was made with government support under contract NAG 5-12429 awarded by NASA. The government has certain rights in the invention.

FIELD OF THE INVENTION

The present invention relates to an immunoisolation patch system, and particularly a patch system comprising multiple immunoisolation microcapsules, each encapsulating biological material such as cells for transplantation. The present invention also relates to methods of using an immunoisolation patch system for the prophylactic and therapeutic treatment of disease in large animals and humans without the need for immunosuppression.

BACKGROUND OF THE INVENTION

Cellular transplantation has recently generated enthusiasm for treating a number of human diseases characterized by hormone or protein deficiencies, such as diabetes, Parkinson's disease, Huntington's disease, liver disease and others. However, a number of technical and logistical challenges have prevented cellular transplantation from working effectively. In particular, transplanted cells must be protected from immune attack by the transplant recipient. This often requires potent immunosuppressive agents having considerable toxicity that can expose the patient to a wide variety of serious side effects. While immunosuppressive agents increase the chance that the host will accept the cell therapy treatment, it has been well documented that immunosuppressive drugs can cause deleterious effects to the host. In particular, immunosuppressive agents lower a subject's resistance to infection, make infections harder to treat, and increase the chance of uncontrolled bleeding. The drugs may also be harmful to the transplanted cells.

An alternative approach is to enclose the transplanted cells within a semi-permeable membrane. In theory, the semi-permeable membrane is designed to protect cells from immune attack while allowing for both the influx of molecules important for cell function and survival and the efflux of the desired cellular product, for example insulin. This immunoisolation approach has two major potentials: i) cell transplantation without the need for immunosuppressive drugs and their accompanying side effects, and ii) use of cells from a variety of sources such as autografts (host stem-cell derived), allografts (either primary cells or stem-cell derived), xenografts (porcine cells or others), or genetically engineered cells.

Macro-immunoisolation systems including intravascular and diffusive devices (e.g., hollow fibers, tubular membranes, flat sandwich pouches, islet sheets, and islet patches) have been tested in diabetic rodents and dogs, and results indicate that many of these systems can function for periods of time. However, these designs have limited application, because implantation is highly invasive surgically, device failure is common, and the side effects of device failure are high. For example, a single breach in macro diffusion devices can cause massive islets death and system failure, and if the breach is sudden, a lethal dose of insulin can be released from the islets, causing death of the host.

Micro-immunoisolation systems, although they overcome many of the problems associated with macro systems, have their own drawbacks. Certain microimmunoisolation systems have been tested in large animal models, but many of those experiments were performed on spontaneous diabetic subjects or utilized immunosuppressive agents. Sun et al. "*Normalization of diabetes in spontaneously diabetic cynomolgus monkeys by xenografts of microencapsulated porcine islets without immunosuppressant*" J. Clin. Invest. 98:1417-22 (1996); Lanza et al. "*Transplantation of islets using microencapsulation: studies in diabetic rodents and dogs*" J. Mol. Med. 77(1):206-10 (1999); R. Calafiore "*Transplantation of minimal volume microcapsules in diabetic high mammalians*" Ann NY Acad. Sci. 875:219-32 (1999); Hering et al. "*Long term (>100 days) diabetes reversal in immunosuppressed nonhuman primate recipients of porcine islet xenografts*" American J. Transplantation 4:160-61 (2004); and Soon-Shiong et al. "*Insulin independence in a Type* 1 *diabetic patient after encapsulated islet transplantation*" Lancet 343: 950-951 (1994). Moreover, many of these experiments could not be reproduced to acceptable scientific standards. The lack of experimental control and consistency of those experiments has complicated scientific interpretation and limited their applicability.

Prior micro-immunoisolation systems have involved the transplantation of encapsulated cells directly into the body cavity of the subject, for example by hypodermic injection or by creating a surgical opening in the body cavity and introducing the encapsulated cells into the body cavity through the opening. Once inside the body cavity, the encapsulated cells could then migrate or diffuse in the body cavity, and may attach to undesirable locations, for example the outer wall of the liver or kidney, which could disrupt the function of those organ, leading to other medical concerns. Micro-immunoisolation systems also suffer from the effects of gravitational sedimentation, which can lead to undesirable system migration and clumping of encapsulated cells within the body, which can cause a number of undesirable side effects and prevent effective functioning of the implant.

Thus, the promise of immunoprotection of living cells to treat hormone-deficient diseases has not been realized. Accordingly, what is needed in the art is a reproducible and effective cell therapy treatment that can be used in large mammals including humans without the use of immunosuppressive drugs.

SUMMARY OF THE INVENTION

The present invention relates to immunoisolation patches for use in cellular transplantation therapy of a disorder, comprising a plurality of multi-membrane microcapsules which encapsulate cellular material and a biocompatible support matrix in which the plurality of multi-membrane microcapsules are distributed, wherein at least some of said plurality of multi-membrane microcapsules comprise at least two membrane layers: an inner membrane biocompatible with the encapsulated cellular material, and an outer membrane which provides chemical stability to the immunoisolation patch system. The disorder can be an endocrine disorder such as diabetes or hypothyroidism, a neurological disorder, or any other disorder able to be treated with cell therapy. Methods of treating (prophylactically or therapeutically) a mammal with the immunoisolation patches are also disclosed. Additional advantages and features of the present invention will be apparent from the following detailed description, drawings and examples, which illustrate preferred embodiments of the invention.

DETAILED DESCRIPTION

Reference will now be made in detail to the presently preferred embodiments of the invention, which, together with the drawings and the following examples, serve to explain the principles of the invention. These embodiments are described in sufficient detail to enable those skilled in the art to practice the invention, and it is to be understood that other embodiments may be utilized, and that structural, biological, and chemical changes may be made without departing from the spirit and scope of the present invention. Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, the preferred methods, devices, and materials are now described.

One skilled in the art may refer to general reference texts for detailed descriptions of known techniques discussed herein or equivalent techniques. These texts include Current Protocols in Molecular Biology (Ausubel et al., eds., John Wiley & Sons, N.Y., and supplements through July 2007), Current Protocols in Immunology (Coligan et al., eds., John Wiley & Sons, N.Y., and supplements through August 2007), Current Protocols in Pharmacology (Enna et al., eds., John Wiley & Sons, N.Y., and supplements through June 2007), The Pharmacological Basis of Therapeutics (Goodman & Gilman, $11^{th}$ ed., 2006), Remington: The Science and Practice of Pharmacy (Lippincott Williams & Wilkins, 21st edition (2005)), Biomedical Aspects of Drug Targeting (Muzykantov & Torchilin, eds., Springer (2003)), Ophthalmic Drug Delivery Systems (A K Mitra, ed., Informa Healthcare, $2^{nd}$ ed. (2003)), Principles and Practice of Ophthalmology (Albert and Jakobiec eds., 2d. ed., W.B. Saunders Company (1999)), and Enhancement in Drug Delivery (Touitou & Barry, eds., CRC Press (2006)) for example.

Figure 1:
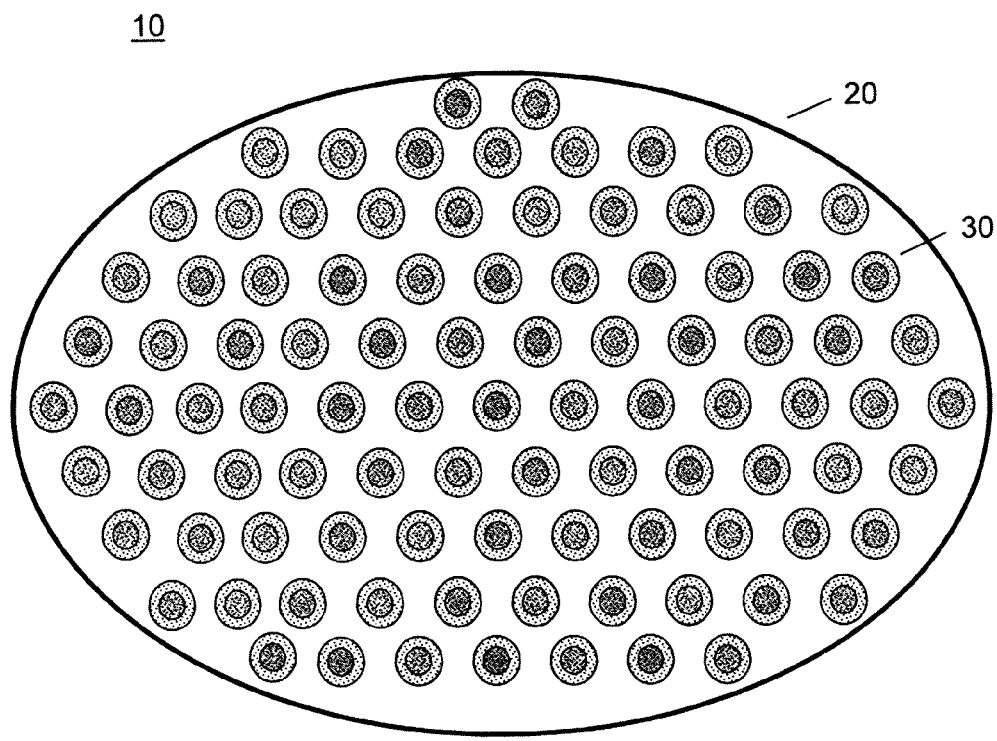
FIG. 1 illustrates an immunoisolation patch of an embodiment of the present invention.

The present invention concerns methods and systems for the prophylactic and therapeutic treatment of disease via cellular transplantation without the need for immunosuppression. As shown in FIG. 1, the immunoisolation patch system 10 of the present invention comprises a support matrix 20, in which a plurality of multi-membrane microcapsules 30, which encapsulate biological material such as cells, are distributed. The microcapsules encapsulate the biological material to be transplanted, and provide stability and immunoprotection benefits to the biological material, thus obviating the need to use immunosuppressive agents. The support matrix provides additional immunoprotection benefits, and retains the microcapsules in proximity to each other and to the site of implantation, thus improving mass transport and safety while preventing microcapsule migration, diffusion, gravitational sedimentation, and clumping. The immunoisolation patch system is small and easily implanted via minimally invasive (e.g., laparoscopic) surgical techniques.

The immunoisolation patch system is useful for cellular transplantation, particularly for the treatment of chronic diseases and disorders such as endocrine disorders. Although it is known to transplant biological material, prior methods have relied either on macro-systems which have limited applications due to safety consideration and invasive surgery for implantation, or on micro-systems which have drawbacks such as migration, diffusion, gravitational sedimentation, or clumping of biological material. The present system, however, may be administered with minimally invasive methods, the microcapsules individually protect small quantities of biological material, and the support matrix retains the relative location of the microcapsules to prevent undesirable movement in the subject after implantation. The advantages of the immunoisolation patch system are particularly beneficial for intra-peritoneal or subcutaneous implantation, as may be particularly desirable for the treatment of endocrine disorders.

A. Multi-Membrane Microcapsules

Figure 2:
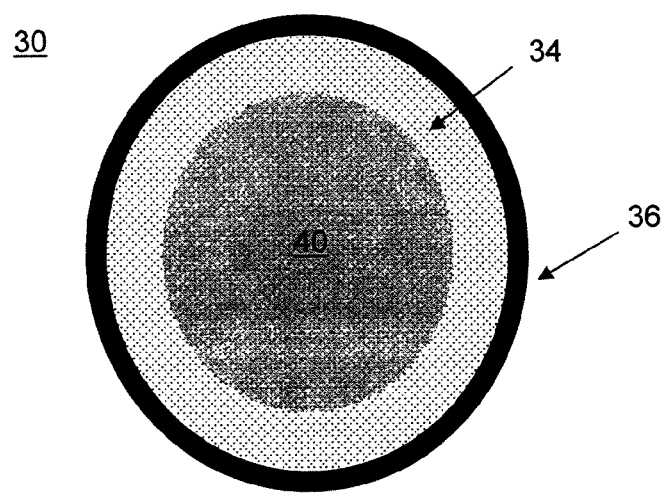
FIG. 2 depicts a multi-layer microcapsule, which encapsulates biological material, of an embodiment of the present invention.

The immunoisolation patch of the invention comprises a plurality of multi-membrane microcapsules, each of which has the ability to encapsulate biological material. As shown in FIG. 2, in a preferred embodiment, a microcapsule 30 comprises an inner membrane 34 and an outer membrane 36, which surround (encapsulate) a biological material 40. The microcapsule may further comprise an additional layer or layers, such as a membrane, coating, or combination of both.

Each membrane performs at least one function in a manner that allows the multi-membrane composition to meet the dichotomy goals of a large-animal transplantation. Although each membrane is designed to allow optimal mass transport while maintaining islet health and functionality, no single membrane is required to compromise its design to meet the multi-faceted dichotomy goals. For instance, increasing the membrane pore sizes to improve mass transfer can jeopardize microcapsule stability, but increasing polymer concentration to improve microcapsule stability can decrease the mass transport. These dichotomies can lead to compromises on microcapsule design and performance. To solve this difficulty, each membrane is designed to perform only one or two specific tasks, and it is the combination of these features in the separate membranes that allows the composition to jointly function in a manner not afforded by a single membrane. Together, the multi-membrane microcapsule meets most or all of the dichotomy goals of cellular transplants in a large animal model without the need for immunosuppression.

The outer membrane of the microcapsule is a thin interwoven membrane with uniform pores that serves as a gatekeeper to keep out most of the high molecular weight immune system components, such as IgM, while allowing low molecular weight oxygen, nutrients, and hormones to pass through without much impedance. The outer membrane possesses sufficient chemical stability to reinforce the inner membrane and the entire microcapsule against chemicals in the host, such as sodium, calcium, magnesium, and potassium ions, as well as other chemicals in the host bloodstream. The outer membrane is chemically stabile against those chemicals, which allows it to retard the deterioration of the membranes. This prolongs the life of the membranes and consequently the biological material that is being enclosed by the inner membrane. The outer membrane also has a relatively uniform pore size, with in combination with its thinness can assist in allowing the membrane to not upset the balance between immunoisolation and mass transport of the inner membrane.

Even if some immune system components pass through the outer membrane, they are still prevented (or at least delayed) from reaching the biological material by the inner membrane, which is thick and has a broad pore size distribution (e.g., it can contains both large and small pores). The numerous small pores in the inner membrane trap the immune system components and act as a barrier membrane. The inner membrane is designed to provide a proper balance between immunoisolation and mass transport. The inner membrane should be biocompatible with the biological material. The term "biocompatible" as used in this context refers to the capability of the implanted composition and its contents to avoid detrimental effects of the host's various protective systems, such as the immune system or foreign body fibrotic response, and remain functional for a significant period of time. In addition, "biocompatible" also implies that no specific undesirable cytotoxic or systemic effects are caused by the composition and its contents such as would interfere with the desired immunoisolation functionality. The inner membrane should also possess sufficient mechanical strength to hold the biological material within the membrane and provide immunoprotection from antibodies in the immune system of a host. The small pores of the inner membrane are designed to prevent or delay most of the immune system from entering the inner sanctum of the microcapsule where the cells reside.

This combination of the inner and outer membranes with different immunoprotection mechanisms protects the biological material from being overwhelmed by the immune system. The outer membrane also acts to bond the inner membrane of the microcapsule with the surrounding material of the support matrix, preferably through affinity binding. Binding the microcapsule membranes and support matrix together in this manner provides a crosslinking effect that creates a tighter and more cohesive immunoisolation patch, and eliminates or reduces the possibility of capsule-immunoisolation patch separation.

In a preferred embodiment, the immunoisolation patch comprises (a) an inner membrane that is biocompatible with the biological material and possesses sufficient mechanical strength to hold the biological material within the membrane and provide immunoprotection from antibodies in the immune system of a host; (b) an outer membrane that possesses sufficient chemical stability to reinforce the inner membrane from the chemicals in the host; and (c) a support matrix that is biocompatible with the host and possesses sufficient mechanical strength to shield the inner and outer membranes from non-specific immune response systems in the immune system of the host.

The relative thickness of the various membranes is selected by the practitioner according to the principles discussed previously. Generally, the thicker the membrane, the more mechanical strength is provided. However, when a membrane becomes too thick, mass transport capabilities start to diminish. In a preferred embodiment, the thickness of the inner membrane is selected from a thickness between about 5 to about 100 microns, more preferably from about 10 to about 60 microns, and most preferably from about 20 to about 40 microns. In another embodiment, the inner membrane has a thickness of about 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 105, 110, 115, or 120 microns. In a preferred embodiment, the thickness of the outer membrane is less than about 5 microns, preferably about 1-3 microns. In another embodiment, the outer membrane has a thickness of about 0.25, 0.5, 0.75, 1, 1.5, 2, 2.5, 3, 3.5, 4, 4.5, 5, 5.5, or 6 microns.

Any combination of these membrane thicknesses may be used, for example in a preferred embodiment, the inner membrane has a thickness of 10-40 microns, the outer membrane has a thickness of 1-3 microns, and the immunoisolation patch has a thickness of 0.6-2.0 mm. In another embodiment, the inner membrane may have a thickness of about 60 microns, the outer membrane may have a thickness of about 3 microns, and the immunoisolation patch may have a thickness of about 0.6-2.0 mm.

In a preferred embodiment, a microcapsule is capable of encapsulating biological material, and comprises (a) a membrane containing sodium alginate, cellulose sulfate, and a multi-component polycation; and (b) a membrane containing a polycation. The first membrane is preferably the inner membrane, and the second membrane is preferably an outer membrane.

In a preferred embodiment, the first membrane should comprise or consist essentially of sodium alginate, cellulose sulfate, and a multi-component polycation. The polycation is preferably a combination of poly(methylene-co-guanidine) and either calcium chloride, sodium chloride, or a combination thereof. This membrane may be the encapsulation system described in U.S. Pat. No. 5,997,900.

The second membrane should comprise a polycation. Any suitable biocompatible polycation may be used, and in a preferred embodiment the polycation is selected from the group consisting of poly-L-lysine (PLL), poly-D-lysine (PDL), poly-L,D-lysine, polyethylenimine, polyallylamine, poly-L-ornithine (PLO), poly-D-ornithine, poly-L,D-ornithine, polyvinylamine, chitosan, cationic polyacrylamide, cationic polyvinyl alcohol, and combinations thereof. More preferably, the polycation is selected from the group consisting of poly-L-lysine, poly-D-lysine, poly-L,D-lysine, poly-L-ornithine, poly-D-ornithine, poly-L,D-ornithine, chitosan, polyacrylamide, poly(vinyl alcohol), and combinations thereof. Most preferably, the polycation is poly-L-lysine. The second membrane also preferably comprises at least one compound selected from the group consisting of sodium alginate, cellulose sulfate, and poly(methylene-co-guanidine). More preferably, the second membrane comprises or consists essentially of a polycation and all three compounds. Most preferably, the second membrane comprises or consists essentially of poly-L-lysine, sodium alginate, cellulose sulfate, and poly(methylene-co-guanidine).

In one embodiment, a microcapsule is capable of encapsulating biological material, and comprises (a) an inner membrane comprising or consisting essentially of sodium alginate, cellulose sulfate, and a multi-component polycation; and (b) an outer membrane comprising or consisting essentially of a polycation. In a preferred embodiment, the multi-component polycation consists essentially of poly(methylene-co-guanidine) and a salt selected from the group comprising calcium chloride, sodium chloride, and combinations thereof; and the outer membrane polycation is a polylysine polycation selected from the group consisting of poly-L-lysine, poly-D-lysine, and poly-L,D-lysine. In another embodiment, a microcapsule has two membranes, and comprises five components. The five components are sodium alginate (SA), cellulose sulfate (CS), polymethylene-co-guanidine (PMCG), calcium chloride ($CaCl_2$), and poly-L-lysine (PLL); the outer membrane comprises or consists essentially of PMCG-CS/PLL-SA, and the inner membrane comprises or consists essentially of PMCG-CS/$CaCl_2$-SA.

In some embodiments, for example when the outer membrane comprises PLL and the inner membrane comprises SA, the PLL component of the outer membrane forms permanent bonds with the SA component of the inner membrane. This interlocking of the two membranes keeps them from separating inside the hostile environment of the intra-peritoneal of large animals. The outer membrane can also provide impedance match for the inner membrane and patch by gradually increasing the polycation concentration outwardly to bind the microcapsules to the support matrix of the immunoisolation patch.

The composition and size of the microcapsules is selected by the practitioner depending on the desired biological material to be encapsulated, and the therapeutic goals. Preferably, the microcapsules have an average diameter ranging from about 15 µm to several mm. Larger sizes are generally preferred when the biological material is of a type that tends to aggregate, for example pancreatic islets or thyroid follicles. In a preferred embodiment, the microcapsules have an average diameter of about 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3200, 3300, 3400, 3500, 3600, 3700, 3800, 3900, 4000, 4200, 4300, 4400, 4500, 4600, 4700, 4800, 4900, or 5000 µm.

The microcapsules can comprise additional layers (e.g., membranes, coatings, or a combination of both). These additional layers may provide better or more enhanced features to those provided by the two-membrane system. The additional layers can, independently or jointly, provide additional immunoprotection, mechanical strength, chemical stability, and/or biocompatibility to the multi-membrane composition. For example, a protective membrane or coating on the outer surface of the microcapsule may provide additional immunoprotection, biocompatibility, and mechanical strength to the microcapsules. Additional layers may be particularly beneficial to use in circumstances where the support matrix may be subjected to damaging forces, because the additional layers can continue to protect individual microcapsules even if the support matrix itself is damaged and unable to provide full protective benefits to the microcapsules. These optional additional layers may be particularly desirable in applications where the microcapsules are used alone (without a support matrix), because the additional layer or layers may provide similar benefits (e.g., immunoprotection) to the microcapsules as the support matrix would.

The multi-membrane composition was designed to be biocompatible, achieve effective mass transport, provide immune protection, provide mechanical strength to the biological material, and provide chemical stability. Biocompatibility of the capsules depends on shielding the immunogenic components of the capsules from the transplantation host. Long-term biocompatibility of the microcapsule membrane was demonstrated when examination of encapsulated islets transplanted into a healthy dog for six and a half months revealed no complications.

Microcapsules can be made with a droplet generator and a chemical reaction chamber, such as that described in U.S. Pat. No. 5,260,002 or 6,001,312. Another droplet generator system is a duo syringe system in which two or more syringes are connected in parallel and submerged in a temperature bath to keep the living cells healthy. The temperature bath containing the syringes may be an ice water bath having a temperature at about 4 degrees C., which aids in keeping the cells in a dormant state. It has been found that islets, when in a dormant state, incur less damage during the transplantation process. This duo syringe system provides continuous operation by allowing for the refilling of one syringe while the experiment is ongoing with the other syringe. The syringes may also contain slow-turning propellers located inside the syringes that assist in maintaining islet density uniformity; i.e., more even distribution of the islets in the syringe.

The chemical reaction apparatus includes a multi-loop chamber reactor that is filled with solution, such as a cation solution. This cation solution bath is fed by a cation stream, which continuously replenishes the solution and carries away the anion drops being introduced into the chamber. Continuous SA/CS droplets can stream from the drop generator, with pancreatic islets enclosed, and enter the cation stream at a designated height and angle; so as to reduce or minimize islet decentering, drop deformation, and air bubble entrainment problems associated with impact. The droplets are then carried into the multi-loop reactor by the polycation stream. The reactor assists in controlling the time of complex formation as well as negating certain gravitational sedimentation effects. The capsules are carried into a second loop reactor with the same or different polycation solution for continuous operation. This facilitates tighter control of microcapsule diameter and sphericity as well as membrane thickness and uniformity. Capsules may be produced with diameters ranging from about 0.5 mm to about 3.0 mm and membrane thicknesses ranging from about 0.006 mm to about 0.125 mm.

The following tests can be performed to optimize the microcapsule and the immunoisolation patch as a whole. Because all the components should work together, it can be difficult to predict how one component will affect another after the immunoisolation patch has been fabricated. For instance, the process of forming the outer membrane can alter the performance of the inner membrane. Likewise, the process of forming the support matrix can alter the performances of the microcapsule membranes. Additionally, advance characterization of each component individually does not predict how the multi-membrane capsules or immunoisolation patches will function together inside transplantation hosts. For these reasons, immunoisolation patch formation was treated and tested as a total system with multiple parameters, e.g., mass transport, immune protection, biocompatibility, sphericity/centering, stability etc.

The mechanical strength of capsules may be measured by placing an increasing uniaxial load on the microcapsule until the microcapsule burst or totally compressed to a flat disc. The mechanical strength of the microcapsule, a function of membrane composition and thicknesses, can be adjusted anywhere from a fraction of a gram to many tens of grams load to meet the transplantation goals without significantly altering the permeability of the microcapsule. Stability of the capsules depends largely on the stability of chemical bonds and the membrane thickness. The intra peritonea fluid of a large animal such as dog can react chemically with the microcapsule membrane and thus weaken the mechanical strength.

Figure 3:
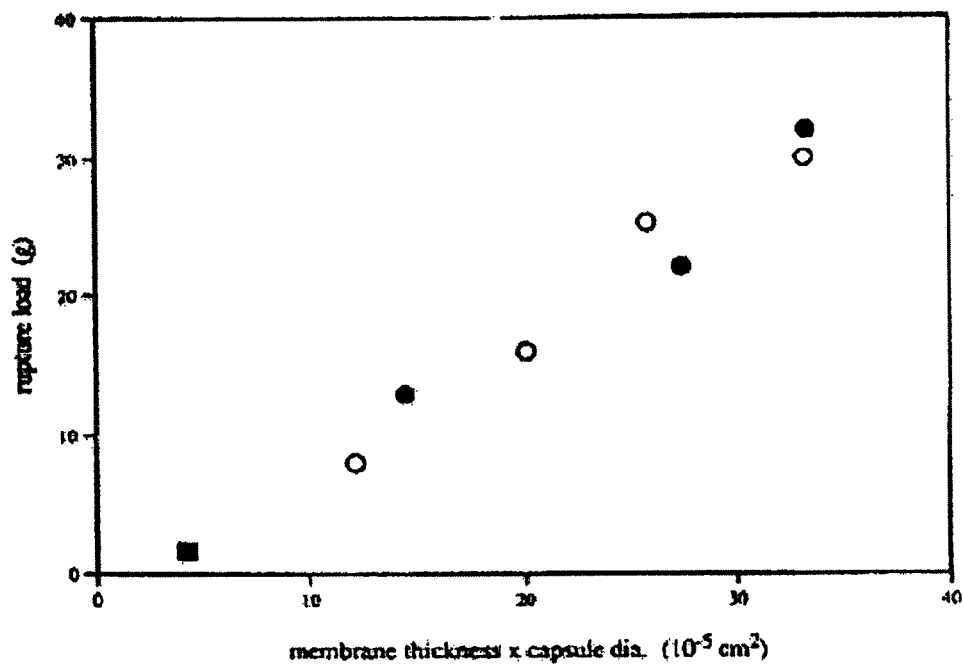
FIG. 3 illustrates microcapsule mechanical stability. The chart illustrates the mechanical strength of capsules of two different polymer concentrations by plotting the rupture load versus the microcapsule membrane thickness and size.

FIG. 3 illustrates the mechanical strength of capsules of two different polymer concentrations by plotting the rupture load versus the microcapsule membrane thickness and size. The slope of the curve represents the rupture stress and thereby indirectly the inherent strength of the capsular membrane. The chart measures mechanical burst strength of capsules by placing them on a uniaxial load. The solid circles represent 0.6-0.6 alginate-CS capsules, the open circles represent 0.9-0.9 alginate-CS capsules, and the solid square represents a PLL-alginate system. As can be seen in the chart, while certain polymers are stronger than others, it is generally observed that thicker membranes tend to be stronger membranes.

Figure 4:
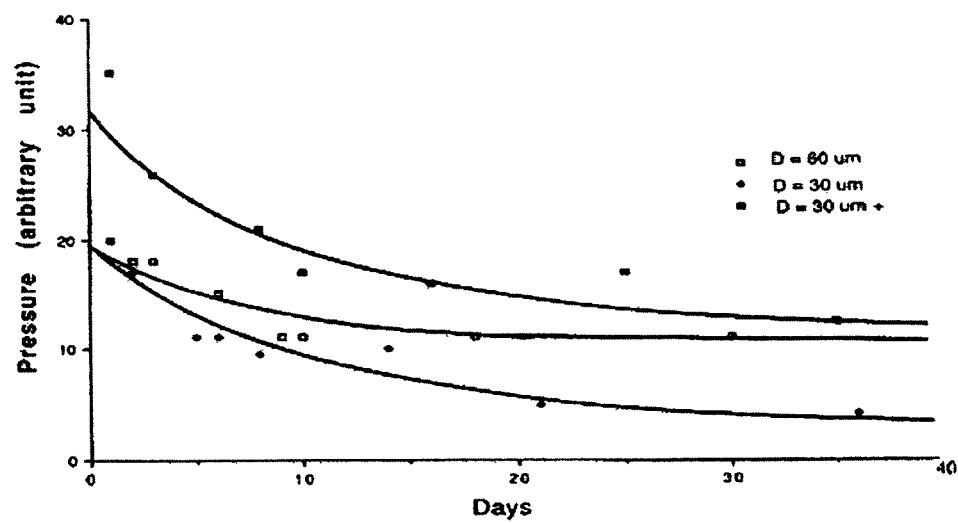
FIG. 4 shows the microcapsule stability. The chart illustrates the mechanical strength of two capsules as a function of time with different chemical compositions and membrane thickness.

FIG. 4 illustrates the mechanical strength of two capsules with different chemical compositions and membrane thickness. The stability was experimentally determined by measuring the length of time for the capsules to lose its mechanical strength by a factor of 1/e incubated in dog serum at 40 degrees C. It is believed that a properly designed microcapsule system can last years in a hostile environment of peritonea of a large animal. In FIG. 4, microcapsule mechanical strength was measured as a function of time as the capsules were incubated in dog serum at 40 degrees C. The solid diamond represent 0.6-0.6 alginate-CS capsules, the solid squares represent 0.9-0.9 alginate-CS capsules, and the open squares represent 0.6-0.6 alginate-CS capsules. Stability is shown by the least amount of fluctuation over time. In the chart, the 0.6-0.6 alginate-CS capsules showed the least amount of fluctuation and would thus be considered the most stable capsules of the three tested.

Figure 5:
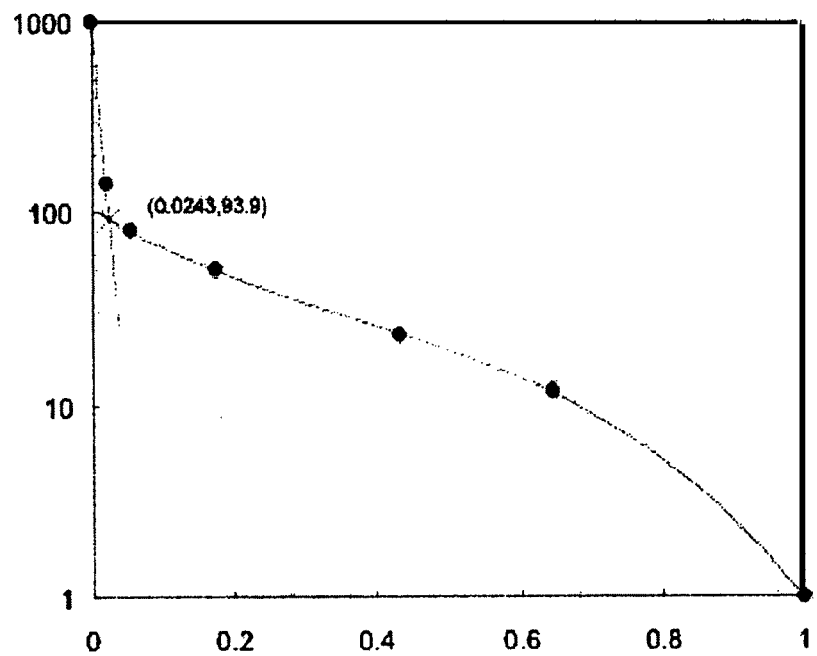
FIG. 5 depicts the permeability of the microcapsule membrane. The chart illustrates normalized retention time as a function of pore size distribution of microcapsule membrane.

In general, the microcapsule is designed to maximize both immune protection and mass transport, but the immune protection goal is inversely proportional to the mass transport goals. It is possible to adjust the parameters to satisfy both goals simultaneously, however, because their power dependences on membrane thickness and pore size are sufficiently different. T. Wang "*New Technologies for Bioartificial Organs.*" Artif. Organs 22(1):68-74 (1998). The membrane pore size can be measured using a size exclusion chromatography (SEC) method. Brissova et al. "*Control and measurement of permeability for design of microcapsule cell delivery system*" J. Biomed. Mat. Res. 39:61-70 (1998). SEC measures the exclusion of dextran solutes from the column packed with microcapsules, and using the measured values of solute size exclusion coefficients (KSEC) and known size of solute molecules, the membrane pore size distribution and microcapsule permeability can be determined. FIG. 5 demonstrates the pore size distribution of a microcapsule membrane with a cutoff of 80 KDa (about 12 nanometers in diameter). This pore size is large enough for glucose and insulin to enter and exit, and small enough to keep the immune system from penetrate all the way to the core of the capsules where biological material reside. The chart illustrates normalized retention time as a function of pore size distribution of microcapsule membrane.

B. Immunoisolation Patch Systems

The microcapsules of the invention are distributed in a support matrix to form an immunoisolation patch. The support matrix retains the microcapsules in proximity to each other and to the site of implantation, thus preventing microcapsule migration, diffusion, gravitational sedimentation, and clumping. It also provides strength to the immunoisolation patch to permit its implantation, removal, re-implantation or transplantation, and the like. The support matrix can be based on any biologically suitable material, and preferably is sufficiently biocompatible with the host such that the host does not treat the patch as a foreign object and reject it or attempt to destroy it. The support matrix (and accordingly the immunoisolation patch) may take a variety of shapes and sizes, for example it may be circular, oval, oblong, triangular, rectangular, pentangular, etc. The support matrix must not alter the performances of the capsules. The support matrix is preferably flexible, so that the immunoisolation patch can conform to the surface contour of the implantation site, and form intimate contact with the tissue at the implantation site to deliver the bioactive agent, so as to receive oxygen, nutrients, and the like for delivery to the biological material inside the microcapsules. A schematic of an exemplary immunoisolation patch is shown in FIG. 1.

Generally, the support matrix provides additional immunoprotection to the microcapsules from the host immune system, improves the biocompatibility of the microcapsule and can also provide additional mechanical strength for stability as well as immune protection. The immunoisolation patch also should possess sufficient mechanical strength to shield the microcapsules from the non-specific innate immune system of the host. The innate immune system, which includes neutrophils, macrophages, dendritic cells, natural killer cells, and others, when activated, can attack the multi-membrane composition or microcapsule by engulfing it. It can also stimulate the activities of antibodies to attack the islets inside of the composition.

The support matrix can be a synthetic polymer-based matrix, or a biopolymer-based matrix. In a preferred embodiment, the support matrix comprises a natural material, preferably natural polymers, which can provide lubrication as well as mechanical strength. Suitable biopolymeric materials include, but are not limited to, proteins (e.g., collagen, gelatin, fibrin, elastin, or silk) and polysaccharides (e.g., hyaluronic acid, alginic acid, alginate, cellulose, chitin). In a preferred embodiment, the support matrix is formed from one or more biocompatible polymers, and preferably comprises a carbohydrate polymer having carboxylate or sulfate groups. The carbohydrate polymer preferably is selected from the group consisting of sodium carboxymethyl cellulose, low methoxy pectins, sodium alginate, potassium alginate, calcium alginate, tragacanth gum, sodium pectate, kappa carrageenans, and iota carrageenans. More preferably, the carbohydrate polymer is selected from the group consisting of sodium alginate, potassium alginate, and calcium alginate. Most preferably, the carbohydrate polymer is sodium alginate.

The support matrix may also comprise an inorganic metal salt. Suitable metal salts include calcium chloride, magnesium sulfate, manganese sulfate, calcium acetate, calcium nitrate, ammonium chloride, sodium chloride, potassium chloride, choline chloride, strontium chloride, calcium gluconate, calcium sulfate, potassium sulfate, barium chloride, magnesium chloride, and combinations thereof. Preferably, the inorganic metal salt is selected from the group consisting of calcium chloride, ammonium chloride, sodium chloride, potassium chloride, calcium sulfate, and combinations thereof. Most preferably, the inorganic metal salt is calcium chloride.

In a preferred embodiment, the immunoisolation patch comprises a plurality of microcapsules, at least some of which comprise (a) an inner membrane that is biocompatible with the biological material and possesses sufficient mechanical strength to hold the biological material within the membrane and provide immunoprotection from antibodies in the immune system of a host, and (b) an outer membrane that possesses sufficient chemical stability to reinforce the inner membrane from the chemicals in the host; and a support matrix that is biocompatible with the host and possesses sufficient mechanical strength to shield the inner and outer membranes from non-specific immune response systems in the immune system of the host.

The immunoisolation patch composition has a porosity that is sufficiently large enough to allow for the release of bioactive agents from the biological material but sufficiently small enough to prevent the entry of antibodies from an immune system. There are known antibodies that destroy living cells that should, when possible, be prevented from entering the multi-membrane composition. For instance, the antibody IgM, which has a molecular weight of about 300 kilodaltons (kDa), can be particularly deadly if it breaches the microcapsules. In view of these known antibodies, the porosity cutoff (i.e., the considerable drop off of the number of pores larger than the cutoff size) of the immunoisolation patch should be less than 300 kDa. Preferably, because membranes are often formulated as a random network system, the porosity cutoff is preferably below about 100 to 150 kDa. This better assures that the designed membrane contains very few or no pores larger than 300 kDa. On the other hand, the porosity cutoff should be larger than about 50 kDa to ensure that bioactive agents released by the biological material have the ability to be freely released from the immunoisolation patch. The porosity cutoff preferably ranges from about 50 kDa to about 250 kDa to permit the passage of molecules having a molecular weight less than about 50 kDa while preventing the passage of molecules having a molecular weight greater than about 250 kDa.

In one embodiment of the invention, each component (e.g., microcapsule inner membrane, microcapsule outer membrane, support matrix) of the immunoisolation patch has about the same porosity. In this embodiment, the porosity cutoff is 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, or 330 kDa, and more preferably is 45, 50, 55, 60, 65, 70, 75, 80, 85, 90, 95, 100, 110, 120, 130, 140, 150, 160, 170, 180, 190, 200, 210, 220, 230, 240, 250, 260 kDa. More preferably, the porosity cutoff ranges from about 80 kDa to about 150 kDa. In another embodiment of the invention, each component has a different porosity. Having components of varying porosity assists, among other areas, in mass transport and immunoprotection. In this embodiment, the porosity cutoff of the inner membrane is 45, 50, 55, 60, 65, 70, 75, 80, 85, 90, 95, 100, 105, 110, 115, 120, 125, 130, 135, 140, 145, 150, 155 or 160 kDa, more preferably in the range of about 50 to about 150 kDa, the porosity cutoff of the outer membrane is 90, 95, 100, 110, 120, 130, 140, 150, 160, 170, 180, 190, 200, 210, or 220 kDa, more preferably in the range of about 100 to about 200 kDa, and the porosity cutoff of the support matrix is 140, 150, 160, 170, 180, 190, 200, 210, 220, 230, 240, 250, 260, 270, 280, 290, 300, 310, 320, 330, 340, or 350 kDa, more preferably in the range of about 150 to about 250 kDa.

In an embodiment of the invention, each component (e.g., microcapsule inner membrane, microcapsule outer membrane, support matrix) of the immunoisolation patch has a narrow pore size distribution, i.e., the pores are of relatively uniform size. In a preferred embodiment, the narrow pore size distribution is characterized by the relation $(d_{50}-d_{10})/d_{50}$ being less than 0.9, 0.8, 0.7, 0.6, 0.5, 0.4, 0.3, 0.2, 0.1 or 0.05, wherein the value $d_{10}$ is the pore diameter at which 10% of the pores are finer, based upon volume, and $d_{50}$ is the median pore diameter. Preferably, the relation $(d_{50}-d_{10})/d_{50}$ is less than 0.5, 0.45, 0.4, 0.35, 0.3, 0.25, 0.2, 0.15, 0.1 or 0.05.

In another preferred embodiment, the pore size distribution of the microcapsule inner membrane is broader than the pore size distribution of the microcapsule outer membrane, for example the relation $(d_{50}-d_{10})/d_{50}$ of the inner membrane can be less than 0.5 but greater than 0.3, and the relation $(d_{50}-d_{10})/d_{50}$ of the outer membrane can be less than 0.3. In this embodiment, the combination of the different pore size distributions of the different components allows for finer adjustments of membrane performance, in that the membranes are able to exclude harmful substances such as IgM from entering without overly hampering mass transport. FIG. 17 depicts the pore size distribution of such an exemplary microcapsule, in which the pore size distribution of the microcapsule inner membrane (dotted line) is broader than the pore size distribution of the microcapsule outer membrane (solid line). The apparent PSD of the capsule membranes was determined by the exclusion of dextran solutes ($K_{sec}$) measurements. The vertical axis ($1-K_{sec}$) approximates pore density of a given size.

The immunoisolation patch may comprise one or more layers of microcapsules. In a preferred embodiment, a monolayer of microcapsules is used, so that each microcapsule can easily participate in mass transport and allow oxygen, nutrients, and hormones to pass through for recipient health. Preferably, the microcapsules are distributed relatively uniformly throughout the support matrix, and are spaced far enough apart to reduce the possibility of hypoxia caused by cells being too close to each other. A relatively thin patch is also desirable to maintain patch flexibility, and to provide a large surface area so that the patch can be kept in place at the implantation site.

The relative size and shape of the immunoisolation patch can be selected by the practitioner according to parameters such as the desired implantation site, the therapeutic application, etc. In a preferred embodiment, the diameter of the patch is about 1, 2, 3, 4, 5, 6, 7, 8, 9, 10, 11, 12, 13, 14, 15, 16, 17, 18, 19, or 20 cm, preferably about 1-10 cm, and more preferably about 3-7 cm, and the thickness of the patch is about 0.25, 0.5, 0.75, 1, 1.25, 1.5, 1.75, 2, 2.25, 2.5, 2.75 or 3 mm thick, preferably about 0.5 to 2 mm thick, and more preferably about 1 mm thick. In a preferred embodiment, the immunoisolation patch is about 6 cm in diameter, and about 1 mm thick. In a preferred embodiment, the immunoisolation patch has a thickness of about 0.4-2.5 mm, more preferably about 0.5-2.2 mm microns, and even more preferably about 0.6-2.0 mm microns.

C. Methods of Treatment

Depending on the disorder to be treated, the microcapsules can be loaded with any suitable biological material. The biological material may be any material that is a capable of being encapsulated by a membrane, and preferably is cellular material, e.g., cells or groups of cells such as acini, follicles, islets, and the like. Typically, the biological material is a cell or group of cells or tissue that can provide a subject with some therapeutic result when introduced into the subject, for example the release of a bioactive agent. The type of cell(s) will vary depending on the disorder to be treated, as is evident to those skilled in the art. For example, in the treatment of liver failure, hepatocytes can be loaded into the microcapsules, and in the treatment of diabetes, pancreatic cells (of one or more types) can be loaded into the microcapsules. The cells may be of the same type or a different type than the native tissue at the site of implantation. For example, in the treatment of a neurological disorder in a human, human neuronal cells may be administered, or non-human cells, such as PC12 cells derived from rats, may be administered.

Cells from a variety of sources can be used, including but not limited to autografts (host stem-cell derived), allografts (either primary cells or stem-cell derived), xenografts (porcine cells or others), or genetically engineered cells. Human biological material, or biological material derived from humans, may be desired if the subject is human, but biological material from other sources, for example cows, pigs, rats, sharks and sheep, may be used. The biological material may be obtained from any suitable source, for example research laboratories, local slaughterhouses, cell cultures, donor tissue, and the like. The number of cells within each microcapsule can be readily controlled by means known to the skilled practitioner. For example, the density of a cell suspension can be varied during formation of the microcapsules to afford microcapsules with varied numbers of cells encapsulated within.

In a preferred embodiment, the biological material is cellular material selected from the group consisting of pancreatic islets, hepatocytes, choroid plexuses, neurons, parathyroid cells, and cells secreting clotting factors. In a preferred embodiment for the treatment of diabetes, the cellular material is pancreatic beta cells, pancreatic islets (Islets of Langerhans), or other insulin-producing islets capable of treating a patient suffering from diabetes. In a preferred embodiment for the treatment of a pancreatic exocrine disorder, the cellular material is centroacinar cells, pancreatic basophilic cells, or acini. In a preferred embodiment for the treatment of a pituitary disorder, the cellular material is a cell of the anterior pituitary gland.

The bioactive agent is any agent that can be released or secreted from the biological material. For example, pancreatic islets have the capability of secreting the bioactive agent insulin; choroid plexuses have the capability of secreting cerebral fluids; neurons have the capability of secreting agents such as dopamine that can effect the nervous system; and parathyroid cells have the capability of secreting agents that can effect metabolism of calcium and phosphorus in a subject. Preferably, the bioactive agent is a hormone or neurotransmitter. In a preferred embodiment for treatment of a pancreatic disorder, the bioactive agent is selected from the group consisting of gastrin, glucagon, insulin, pancreatic polypeptide, and somatostatin, and preferably is insulin. In another preferred embodiment for treatment of a pancreatic disorder, the bioactive agent is selected from the group consisting of chymotrypsin, pancreatic amylase, pancreatic lipase, and trypsin. In a preferred embodiment for treatment of a thyroid disorder, the bioactive agent is selected from T1, T2, T3, T4, and calcitonin. In a preferred embodiment for treatment of a neurological disorder, the bioactive agent is a neurotransmitter, and preferably is dopamine.

The various embodiments of the present invention have a wide variety of therapeutic and prophylactic uses in the area of cell therapy or cellular transplantation, for example in the treatment of age-related disorders, allergic disorders, autoimmune diseases, cancers, endocrine disorders, immune disorders, inflammatory disorders, neurological disorders, organ failure, proliferative disorders, other conditions involving tissue injury, and other conditions wherein replacement cells are desirable.

As known in the art, cell therapy is the transplantation of human or animal cells to replace or repair damaged or malfunctioning tissues, and/or cells. The types of cells that are administered correspond in some way with the organ or tissue in the patient that is failing. For example, in the context of a subject suffering from diabetes or related disorders, cell therapy treatment involves the transplantation of insulin-producing cells that can replicate the function of pancreatic cells and release insulin into the subject upon the advent of certain conditions, namely an elevated glucose level in the subject. The cells can be introduced through implantation, transplantation, injection or other means known in the art.

The administration of the patches of the present invention may be for a "prophylactic" or "therapeutic" purpose. The administration is said to be for a "therapeutic" purpose if the amount of biological material administered is physiologically significant to provide a therapy for an actual manifestation of the disease. When provided therapeutically, the patch is preferably provided at (or shortly after) the identification of a symptom of actual disease. The therapeutic administration serves to attenuate the severity of such disease or to reverse its progress. The administration is said to be for a "prophylactic" purpose if the amount of biological material administered is physiologically significant to provide a therapy for a potential disease or condition. When provided prophylactically, the patch is preferably provided in advance of any symptom thereof. The prophylactic administration serves to prevent or attenuate any subsequent advance of the disease.

Providing a therapy or "treating" refers to any indicia of success in the treatment or amelioration of an injury, pathology or condition, including any objective or subjective parameter such as abatement, remission, diminishing of symptoms or making the injury, pathology or condition more tolerable to the patient, slowing in the rate of degeneration or decline, making the final point of degeneration less debilitating, or improving a patient's physical or mental well-being. The treatment or amelioration of symptoms can be based on objective or subjective parameters, including the results of a physical examination, neuropsychiatric exams, and/or a psychiatric evaluation. For example, the methods of the invention successfully treat a patient's diabetes by stabilizing the patient's blood glucose levels, which is evident upon administration of a blood glucose assay.

Preferred subjects for treatment include animals, most preferably mammalian species such as humans, and domestic animals such as dogs, cats and the like, subject to disease and other pathological conditions. A "patient" refers to a subject, preferably mammalian (including human), and preferably a large mammal. In a preferred embodiment, the patient is a human.

In a preferred embodiment, the immunoisolation patch is used as a hormone-producing system, which can be used to treat, e.g., an endocrine disorder. For example, a pancreatic disorder can be treated by implanting an immunoisolation patch comprising one or more types of pancreatic tissue or cells such as alpha cells, beta cells, centroacinar cells, delta cells, epsilon cells, pancreatic basophilic cells, PP cells (F cells), acini, or Islets of Langerhans into a patient. Similarly, a thyroid disorder can be treated by implanting an immunoisolation patch comprising one or more types of thyroid tissue such as thyroid epithelial cells (follicular cells), parafollicular cells, or follicles into a patient.

Exemplary endocrine disorders that may be treated by various embodiments of the present invention include, but are not limited to adrenal disorders, including but not limited to adrenal insufficiencies such as Addison's disease, congenital adrenal hyperplasia (adrenogenital syndrome), and mineralocorticoid deficiency, Conn's syndrome, Cushing's syndrome, and pheochromocytoma; autoimmune polyendocrine syndromes, including but not limited to Type 1 autoimmune polyendocrine syndrome, Type 2 autoimmune polyendocrine syndrome (Schmidt's syndrome), and immunodysregulation polyendocrinopathy enteropathy X-linked syndrome (IPEX or XPID); glucose homeostasis disorders, including but not limited to diabetes mellitus, hypoglycemia, and idiopathic hypoglycemia; metabolic bone diseases, including but not limited to osteoporosis, osteitis deformans (Paget's disease of bone), rickets and osteomalacia; pancreatic disorders, including but not limited to diabetes mellitus, exocrine pancreatic insufficiency, hypoglycemia, pancreatitis, and Shwachman-Diamond Syndrome; parathyroid gland disorders, including but not limited to primary hyperparathyroidism, secondary hyperparathyroidism, tertiary hyperparathyroidism, hypoparathyroidism, and pseudohypoparathyroidism; pituitary gland disorders, including but not limited to diabetes insipidus, growth hormone deficiency, hypopituitarism (or panhypopituitarism), Sheehan syndrome, and syndrome of inappropriate antidiuretic hormone; sex hormone disorders, including but not limited to amenorrhea, infertility, hypogonadism, gonadotropin deficiency, Kallmann syndrome, Klinefelter syndrome, menopause, menstrual function disorders, ovarian failure, polycystic ovary syndrome, testicular failure, and Turner syndrome; and thyroid disorders, including but not limited to hyperthyroidism, hypothyroidism, and thyroiditis, for example acute thyroiditis, De Quervain thyroiditis, Graves-Basedow disease, Hashimoto's thyroiditis, Hashitoxicosis, iatrogenic hyperthyroidism, iatrogenic hypothyroidism, Ord's thyroiditis, postoperative hypothyroidism, postpartum thyroiditis, silent thyroiditis, thyroid storm, toxic nodular struma (Plummer's disease), and toxic thyroid nodule.

Exemplary cancers of the endocrine organs that may be treated by various embodiments of the present invention include, but are not limited to adrenal hyperplasia or neoplasia, adrenocortical carcinoma, insulinoma, pituitary tumors such as pituitary adenomas, prolactinoma (or hyperprolactinemia), acromegaly (gigantism), and Cushing's disease, thyroid tumors such as thyroid adenoma, anaplastic thyroid cancer, follicular thyroid cancer, medullary thyroid cancer, and papillary thyroid cancer, and endocrine tumor syndromes such as Carney Complex, McCune-Albright syndrome, von Hippel Lindau syndrome (VHL syndrome), and multiple endocrine neoplasia (multiple endocrine adenomatosis) or MEN syndromes such as Wermer syndrome (MEN 1), Sipple syndrome (MEN 2A), MEN 2B, and FMTC.

In a preferred embodiment, the disorder to be treated is diabetes, including but not limited to, Type 1 diabetes, Type 2 diabetes, maturity-onset diabetes of the young (MODY), latent autoimmune diabetes adult (LADA), impaired glucose tolerance (IGT), impaired fasting glucose (IFG), gestational diabetes, and metabolic syndrome X. Preferably, the disorder to be treated is Type 1 diabetes or Type 2 diabetes.

A variety of administration routes for the compositions of the present invention are available. The particular mode selected will depend, of course, upon the particular biological material selected, whether the administration is for prevention, diagnosis, or treatment of disease, the severity of the medical disorder being treated and the desired therapeutic efficacy. The duration of prophylactic and therapeutic treatment will also vary depending on the particular disease or condition being treated. Some diseases lend themselves to acute treatment whereas others require long-term therapy. Generally, the immunoisolation patches are surgically implanted, for example laparoscopically, into an appropriate location in the body, and may be loosed placed therein or affixed to the surrounding tissue. For example, an immunoisolation patch used for the treatment of diabetes may be surgically placed intra-peritoneally in the abdomen and on the surface of the omentum, or in subcutaneous locations.

In an embodiment for the treatment of diabetes or related disorders, a method of treatment comprises implantation of an immunoisolation patch comprising multi-membrane microcapsules encapsulating insulin-producing islet cells that provides a sustained release of insulin for at least 30 days. The patch does not exhibit significant degradation during the sustained-release period. The term "sustained release," as used herein, refers to the continual release of the biological agent from the biological material during instances when the release should take place. For instance, if the biological material is a pancreatic islet and the biological agent is insulin, the pancreatic islets should, after transplantation, continually release insulin into the host any time the pancreatic islets recognize that the glucose level of the host has reached a certain point. After the glucose level in the host has been maintained, the pancreatic islets will temporarily cease secreting additional insulin. However, when the glucose levels in the host again reach a point where insulin is needed, the temporarily-dormant pancreatic islets will again begin to secrete insulin. This type of continual release is an example of sustained release.

The sustained-release period should last at least 30 days. Preferably, it lasts at least 60 days; more preferably, at least 120 days; and most preferably, at least 180 days. The longer the composition is able to provide a sustained release of insulin, the longer the patient will be functioning on the cell therapy treatment alone without needing additional treatment. For instance, if the cell therapy treatment is able to last for at least 180 days, a patient will only need to receive a booster treatment approximately once every six months. This allows a diabetic patient a significantly increased amount of freedom to pursue daily activities without having to continually monitor their disorder and correct for high or low blood sugars and take insulin by injection or otherwise to counterbalance carbohydrate intake and regular and continual release of glucose into the bloodstream by the liver. This will also allow for overall greater glycemic control by reducing the occurrence of insulin shock or ketoacidosis as well as preventing or delaying the onset of diabetic related complications.

This invention also relates to a method of stabilizing the glucose level in a patient for at least 30 days, comprising administering to a patient suffering from diabetes or related disorders an immunoisolation patch containing multi-membrane microcapsules encapsulating insulin-producing islet cells. The method can stabilize the glucose level for at least 30 days; preferably, at least 60 days; more preferably, at least 120 days; and most preferably, at least 180 days.

Application of the teachings of the present invention to a specific problem or environment is within the capabilities of one having ordinary skill in the art in light of the teachings contained herein. Examples of the products and processes of the present invention appear in the following examples.

Example 1

Pancreatic Islet Isolation and Evaluation

For the isolation of pancreatic islets, mongrel canines (20-28 kg body weight) were placed under general anesthesia following an 18-hour fast. A midline laparotomy was performed. The gastroduodenal, splenic and pancreaticoduodenal veins and arteries were isolated and a ligature was placed around each vessel. The main pancreatic duct was identified at the point of duodenal entry and dissected. A ligature was placed around the duct. An 18-gauge angiocath was inserted into the duct and the tip advanced 2-3 mm such that it remained in the main ductal architecture just prior to ductal branching in the pancreas. The catheter was sutured to the duct to secure its position. Immediately prior to harvest, the previously placed vascular ligatures were tightened and the animal was euthanized. The pancreas was transected from all peritoneal and vascular attachments and dissected from the duodenum. Once excised, the pancreas was immediately perfused with ice-cold University of Wisconsin (UW-D) perfusion solution via the previously placed ductal catheter.

A visual inspection was performed to ensure that the entire pancreas is perfused. The harvested glands were transported on ice to the laboratory where the UW-D solution was replaced by a solution of collagenase in UW-D (Crescent Chemical). The glands were then placed in a shaking water bath and digested at 40° C. for approximately 35 minutes. The dissociated tissue was filtered through a 400 µm mesh screen and washed several times with ice-cold media to remove and inactivate the collagenase. Based on density differences between islets and exocrine tissue, a discontinuous ficoll gradient was used to separate the islets and exocrine tissue. After density centrifugation, the islets were collected, washed, and transferred to tissue culture M199 media supplemented with 10% FBS (Fetal Bovine Serum) and antibiotics. During culture for 48-72 hours, isolated islets maintained their compact appearance and the microcapsule surface remained smooth.

Islet isolations were performed on 56 canine pancreases. A profile of the average isolation results per pancreas is shown below (islets fragments that are smaller than 50 µm are not quantified). In addition to the number of islets isolated, the quality of isolations was evaluated by determining the islet diameter, purity, islet viability, and islet function. Since the average islet diameter will vary, the isolation yield is normalized by computing the ratio of the average islet volume and the volume of a "standard" islet of 150 µm in diameter. The resulting value is referred to as the Equivalent Islet Number (EIN) and allows a yield-comparison for different isolations. Islet purity was determined from a sample that was stained with the islet-specific dye dithizone. The dye stains islets red but leaves exocrine tissue unstained. Most of the exocrine tissue dies during the first 24 hrs of culture, resulting in an increase in purity during culture to approximately 95%.

Islet viability is determined from a sample that was stained with a combination of Calcein AM (stains live cells fluorescent green) and Ethidium Bromide (stains the nuclei of dead cells fluorescent red). Viability is scored on a scale of 1 (all cells dead) to 4 (all cells alive). The average of five typical isolations is tabulated below.

| | |
|---|---|
| Islets per pancreas | 435 ± 38K |
| Islet Diameter | 106 ± 3.8 µm |
| Islet Equivalent Number | 0.48 ± 0.04 |
| Purity | 87.3 ± 1.2% |
| Viability | 3.5 ± 0.1 |

Example 2

Microcapsule Formation

A series of capsules having a range of permeability (porosity cutoff ranging from 40 kDa-230 kDa, based on dextran exclusion measurement) was developed and characterized. The apparent pore size of the capsular membrane was determined by size exclusion chromatography (SEC) that measures the exclusion of dextran solutes from a column packed with microcapsules. Measuring permeability as a function of polymer component concentration and chemical reaction time allowed adjustment of microcapsule permeability in a controlled manner. Two-membrane microcapsule was formed. The outer membrane with strong ionic bonds formed a thin membrane with narrow pore size distributions. It has a porosity of ~100 kDa and thickness of ~1 micron. The inner membrane of this capsule is thicker and its pore size has broad distributions. It has a porosity of approximately 150 kDa and thickness of 20-40 microns.

Three-membrane microcapsules were also formed, in which the inner membrane has a porosity of approximately 150 kDa and thickness of 20-40 microns, the outer membrane has a porosity of approximately 100 kDa and thickness of 1-3 microns, and the additional (outermost) membrane has a porosity of approximately 250 kDa and thickness of 100-300 microns. Also formed were three-layered microcapsules having these porosity and thickness ranges, in which the inner membrane is PMCG-CS/CaCl$_2$-SA, the outer membrane is a thin interwoven PMCG-CS/PLL-SA, and the additional membrane is CaCl$_2$-SA.

Example 3

Encapsulation of Pancreatic Islets and Testing

Pancreatic islets were isolated as described in Example 1, and following islet isolation, diameter, purity, and viability testing, the islets were cultured for 48-72 hours and encapsulated with a multi-membrane microcapsule of Example 2. The insulin secretory capacity of the free islets and encapsulated islets was then determined in a cell perfusion system.

Insulin secretion by encapsulated islets was evaluated in a cell perfusion apparatus with a flow rate of 1 ml/minute with RPMI 1640 with 0.1% BSA as a perifusate. Encapsulated islets were perifused with 2 mM glucose for 30 minutes and the column flowthrough discarded. Three minute samples of perifusate were collected during a 30 minute perfusion of 2 mM glucose, a 30 minute perfusion of 20 mM glucose+0.045 mM IBMX (a nutrient), and a 60 minute perfusion of 2 mM glucose. Samples were assayed in duplicate for insulin using Coat-a-Count kits (Diagnostic Products Corporation, Los Angeles, Calif.) with a canine insulin standard. The amount of insulin secreted was normalized for the number of islets.

Figure 6:
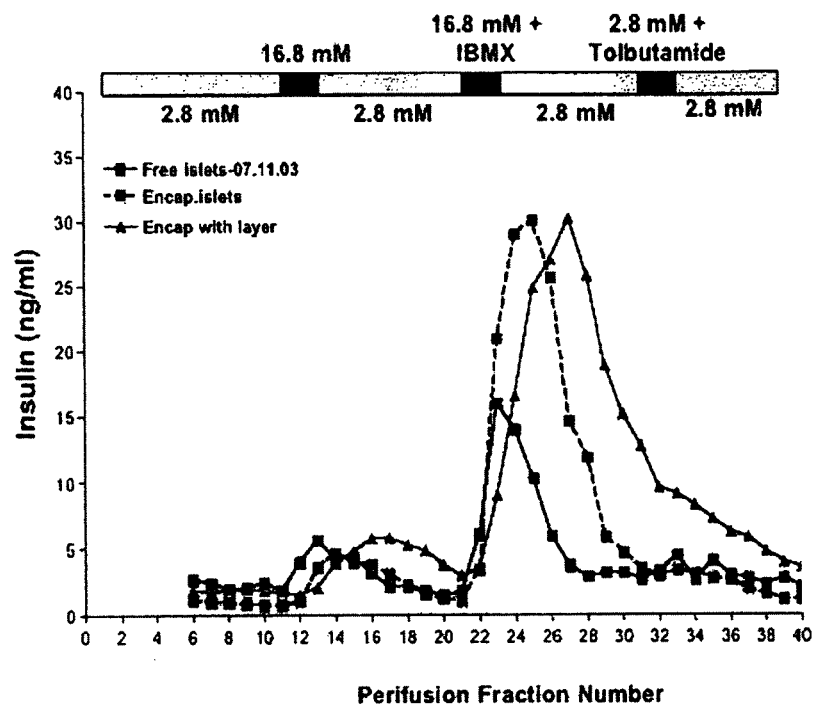
FIG. 6 depicts the perfusion of encapsulated islets. The secretion level of insulin-releasing islets was assessed in a cell perfusion system. Free islets (not encapsulated), islets encapsulated in a single-membrane system (encapsulated islets), and islets encapsulated in a multi-membrane system (encapsulated with layer) were independently assessed.

As assessed by the dynamic response to insulin secretagogues, insulin secretion by encapsulated islets had a similar profile as unencapsulated free islets with a slightly delay in insulin secretion, as shown in FIG. 6. This delay in insulin secretion and the cessation of insulin secretion following removal of the stimulus reflects (a) the time for the secretagogue to enter the microcapsule and reach the islet and (b) the time for insulin to exit the microcapsule. FIG. 6 depicts a cell perfusion system measuring the secretion level of insulin-releasing islets. Free islets (not encapsulated), islets encapsulated in a single-membrane system (encapsulated islets), and islets encapsulated in a multi-membrane system (encapsulated with layer) were independently assessed. Stimuli for insulin secretion are shown in the black bars at the top of the graph. Insulin in perfusion fractions collected every 3 minutes was quantified by radioimmunoassay. The number of islets was not normalized, so the focus of the chart should lie on the response time rather than the height of the graphs. The similarity of the response time in the three graphs with only minute delays suggests that the islets encapsulated in the multi-membrane system will function normally inside transplanted animals.

Example 4

In Vivo Testing of Microcapsules in Pancreatectomized Canines

The biocompatibility and functional capacity of the multi-membrane encapsulated islets has been studied in a pancreatectomized canine model. The animal's size and hence blood volume permits the daily evaluations of plasma glucose and insulin, clinical assessments of glucose tolerance and evaluations of biocompatibility and safety. In addition, the canine model is widely utilized model of human glucose homeostasis and diabetes. Total pancreatectomy in the canine results in complete absence of endogenous insulin and thus assessments of insulin concentration can be directly assessed to the function and responsiveness of the encapsulated islets.

Mongrel canines of either sex with a mean wt of 7.6 kg were studied. The animals were housed in a facility that met the American Association for the Accreditation of Animal care guidelines. All animal care procedures were reviewed and approved by the University of Vanderbilt's Institutional Animal Care and Use Committee. Seventeen to twenty four days prior to encapsulated islet intraperitoneal administration, a total pancreatectomy was performed as described below. In the post-operative period animals are fed a standard diet of chow and canned diet (34% protein, 14.5% fat, 46% carbohydrate, and 5.5% fiber) based on dry weight. Exocrine pancreatic enzymes, lipase (70,000 U), amylase (210,000 U) and protease (210,000 U) were administered along with their meal in order to assist in food digestion and compensate for the absence of exocrine pancreatic function. Animals received daily insulin injections in adjusted dosages to maintain euglycemia at 12 hours post feeding without glycosuria during 24 hours. The insulin requirements generally range from 0.6-0.9 U/kg Regular Pork and 1.0-1.3 U/kg NPH Pork, q 24 hr.

After pancreatectomy, daily insulin requirements were allowed to stabilize. On the day of encapsulated islet administration, exogenous insulin is withheld and blood-glucose levels were monitored. Animals were fasted 12 hours and placed under general anesthesia using propofol (4.4 mg.kg, IV) and Isoflurane (2.0% with O$_2$, inhalation). A 1.5 cm midline laparotomy was performed and a 7.0 mm I.D. cannula is inserted into the peritoneal space. A funnel is connected to the free end of the cannula. Encapsulated islets prepared as described in Example 2 and suspended in modified Hanks solution containing canine albumin were administered into the abdominal space at room temperature. Total administered packed volume of capsules was 150-200 ml. The intraperitoneal cannula was immediately removed and the laparotomy incision closed. The animal was allowed to recover and immediately fed her/his daily ration. The ration was consumed within 2 hours from the time of the encapsulated islet administration. Six to eight hours post administration of food, blood was collected for the assessment of glycemic status and daily collections were performed thereafter for 3 days. No immune-suppressive drugs were administered to the animals.

Following the immediate post-administration period, animals were fed the standard daily rations and blood collections were performed on 2-3 day intervals for the determination of glucose and insulin. At the time of blood collections, animals were weighed and general physical conditions were assessed. An oral glucose tolerance test was performed at 2-4 weeks following encapsulated islet administration. Following an 18-hour fast, an 18-gauge angiocath was placed into either the left or right jugular vein for the collection of blood. Dextrose (0.7 gm/kg) was administered orally following the collection of a baseline blood sample. Blood samples were collected at 2.5-minute intervals for the first 20 minutes and 5 and 10-minute intervals thereafter for the 3-hour duration of the test. Plasma glucose levels were determined by the glucose oxidase method using a Beckman Glucose II analyzer (Beckman Instruments Palo Alto Calif.). Plasma insulin was determined by radioimmunoassay using a double-antibody system.

Figure 7:
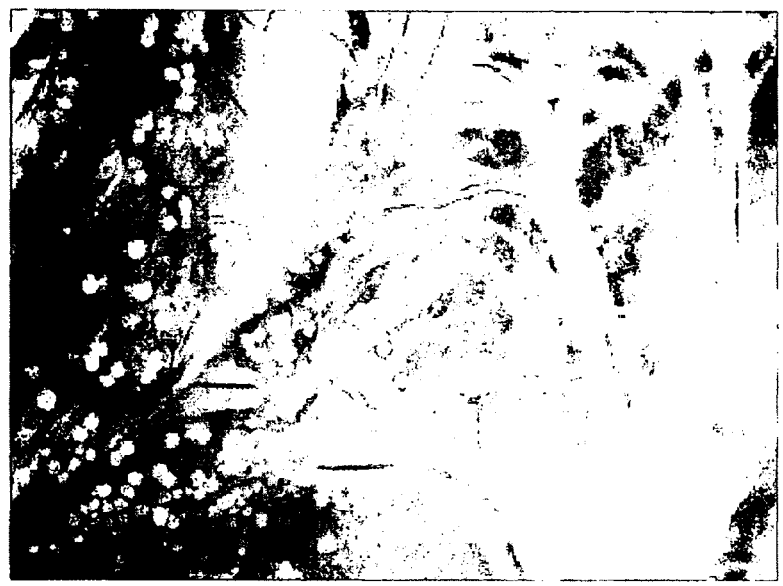
FIG. 7 shows the biocompatibility of multi-membrane microcapsules in a large animal. The omentum of normal dog is shown more than six months after treatment having microcapsules loosely adhered to the omentum.

FIG. 7 depicts the omentum of normal dog shown more than six months after treatment (dog received encapsulated islets on Feb. 14, 2001 and was sacrificed on Aug. 14, 2001). Before sacrifice, no complications were observed in the animal, and post sacrifice, no abnormalities were observed in or on the organs. The figure shows minimal inflammatory response and mild vascularization of the omentum. A few capsules (less than 1%), were observed to contain a scant amount of fibrin and rare mononuclear cells adherent to the surface. The surface of the vast majority of capsules retrieved from the dog were clean and transparent, and barely visible with the naked eye but readily apparent under microscope. Evidence of tissue reactivity has been minimal. There was no observed involvement of any other organ system in the splanchnic bed. The capsules loosely adhered to the omentum and were easily washed off, indicating that the capsules were anchored but not imbedded in the omentum. Microcapsule integrity was excellent with minimal microcapsule "breakage" observed. The retrieved encapsulated islets removed after six and a half months were still alive.

Example 5

In Vivo Testing of Microcapsules in Diabetic Canines

Using the total pancreatectomy dog model, the function and safety of the intra-peritoneally administered microcapsules encapsulating canine islets (allograft) was assessed in 10 diabetic animals. Canines were prepared, and microcapsules implanted, as described in Example 4. The recurrence of diabetes, as determined by a glucose level of greater than 180 mg/dl for 4 consecutive days, occurred in dog 1 at approximately 100 days post transplantation.

Figure 8:
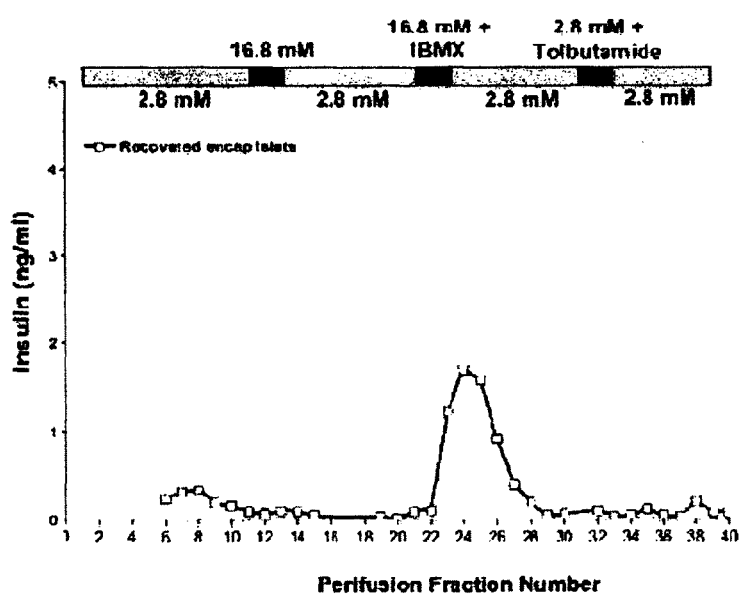
FIG. 8 illustrates insulin secretion by retrieved encapsulated islets. Islets encapsulated in a multi-membrane microcapsule retrieved after being transplanted in a dog at 100 days post transplantation were tested in a cell perfusion system.

Encapsulated islets were retrieved and tested in the cell perfusion system using the same stimuli as described in Example 3. Results are shown in FIG. 8. The chart in FIG. 8 indicates that the encapsulated islets are still viable as evidenced by the response to a high glucose plus IBMX, but have reduced insulin secretory capacity. These results suggest that the diabetes recurred because of inadequate islet mass and further suggest that this is due to reduced islet mass or function that is not the result of an allograft reaction.

Figure 9:
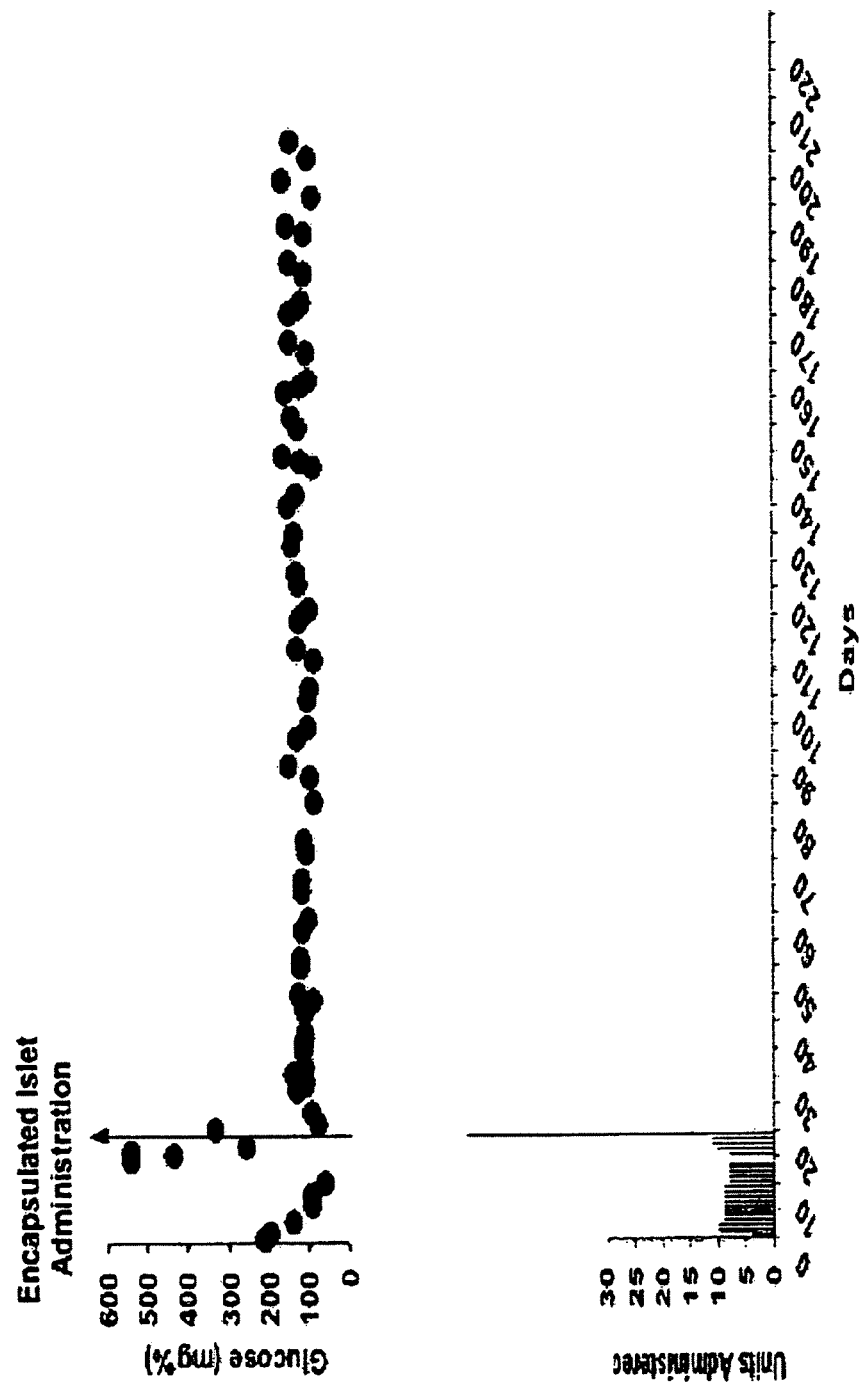
FIG. 9 shows blood glucose analysis of canine allotransplantation. The figure is an example of a canine model that has undergone a total pancreatectomy. The top panel illustrates the venous plasma glucose concentrations collected 12-18 hours following a meal. The lower panel illustrates the daily dosage of subcutaneous porcine insulin administered.
Figure 10:
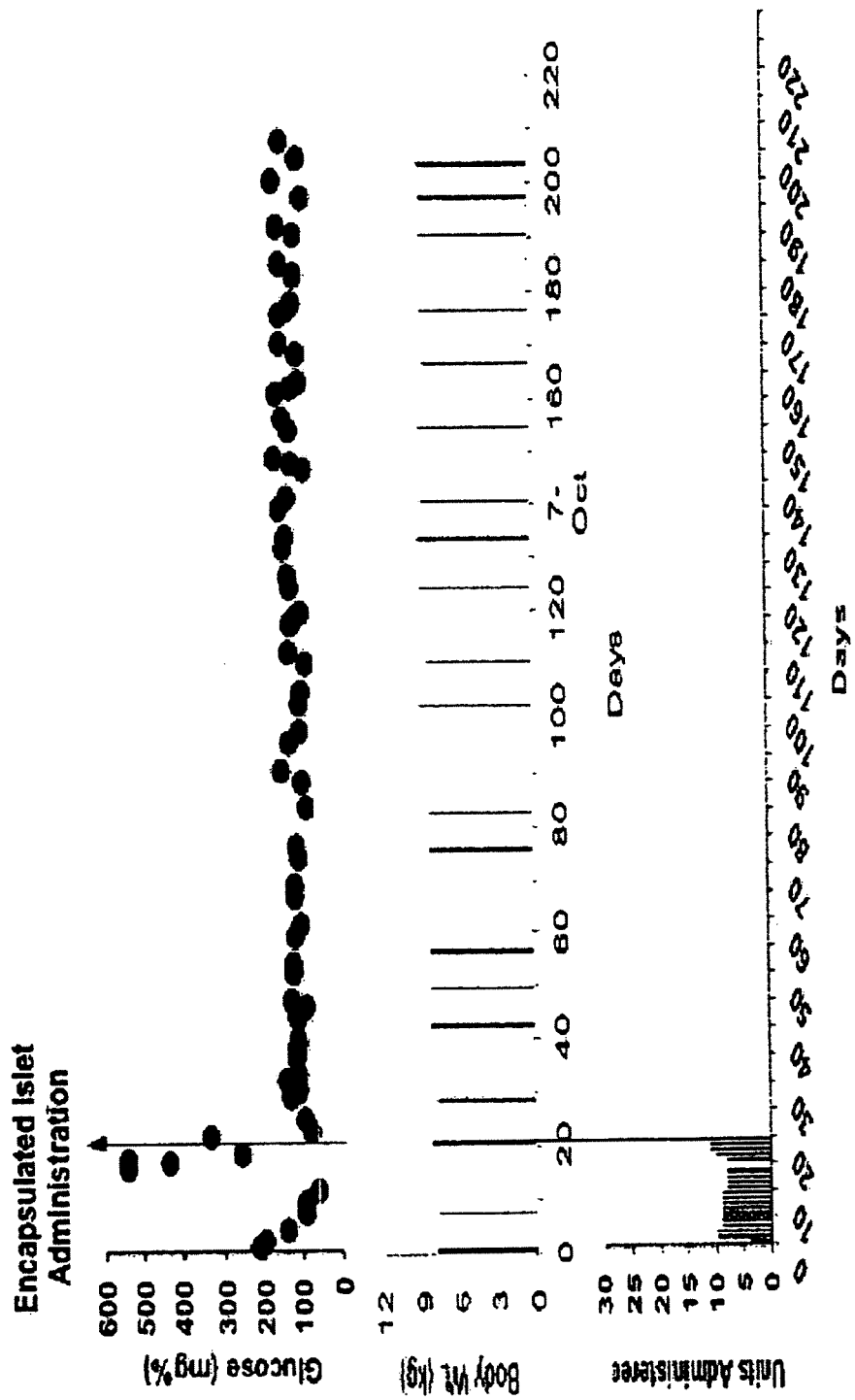
FIG. 10 depicts the body weight analysis of canine allotransplantation. The top and bottom panels have been imported from FIG. 9. The middle panel shows the animal body weight monitored during the testing period.
Figure 11:
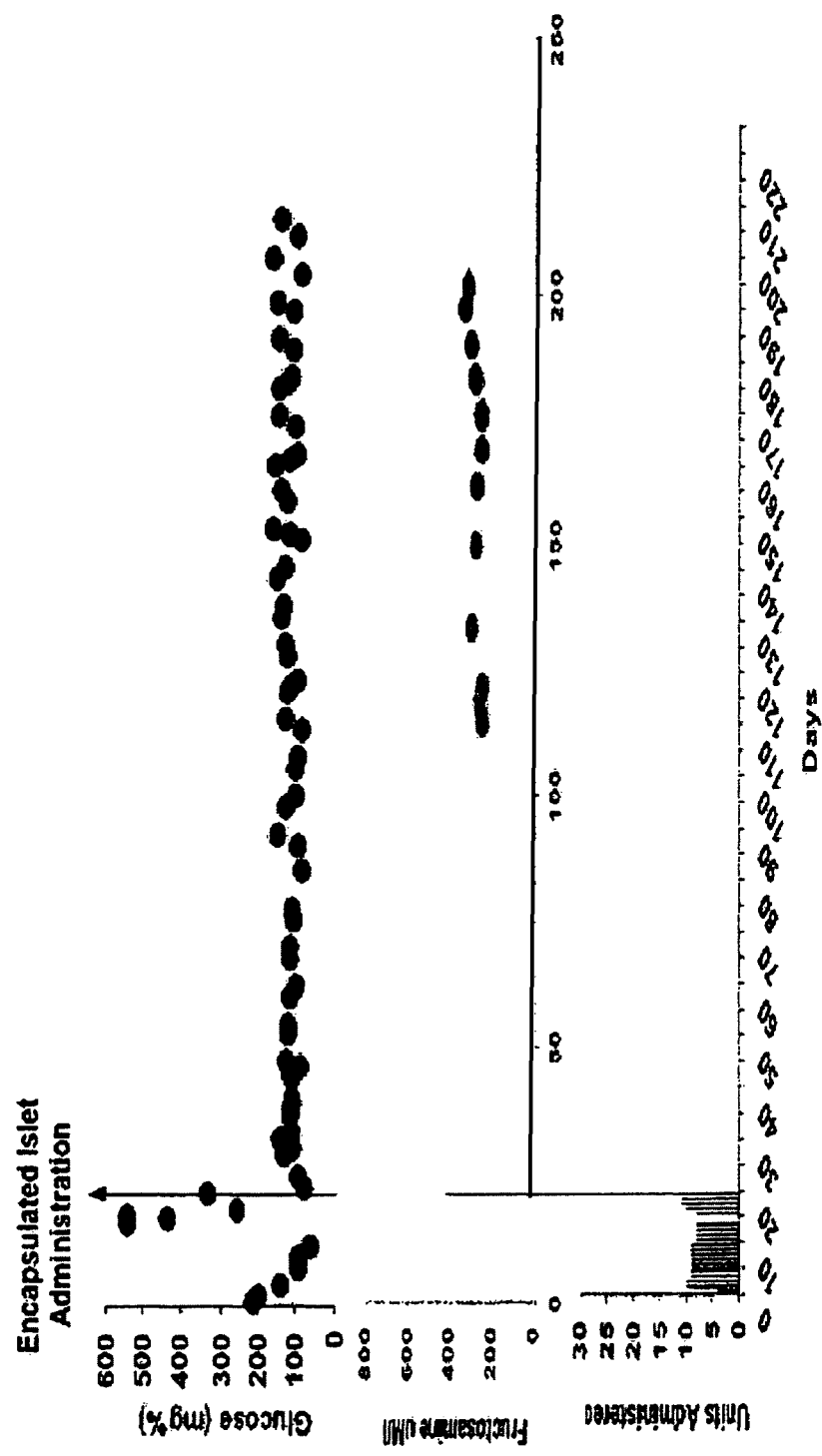
FIG. 11 illustrates fructosamine analysis of canine allotransplantation. The top and bottom panels have been imported from FIG. 9. The middle panel shows fructosamine measurements, an indicator of blood glucose level averaged over 2-3 weeks in diabetic subjects.

Fasting glucose concentrations, body weight, and fructosamine measurements of dog 10 are shown in FIGS. 9-11 as representative data. The retrieved capsules were clean and intact, suggesting that the longevity of the transplant is no longer limited by the microcapsule stability, but rather the loss of islet mass. FIG. 9 depicts blood glucose analysis of canine allotransplantation. Transplantation of islets encapsulated in a multi-membrane system has demonstrated the efficacy in reversing diabetes in a canine model (dog no. 10) that has undergone a total pancreatectomy. The top panel illustrates the venous plasma glucose concentrations collected 12-18 hours following a meal. The lower panel illustrates the daily dosage of subcutaneous porcine insulin administered. The upper portion of bar in the lower panel indicates NPH insulin and the lower portion of bar indicates regular insulin. In days 18 and 19, treatments ceased to verify that the dog was diabetic. As seen in the top panel, glucose level rose dramatically when insulin treatments ceased. Insulin treatments resumed on day 20. On the morning of day 25, insulin treatments again ceased. In the afternoon of day 25, islets encapsulated in multi-membrane system were transplanted into the canine, as indicated by the vertical line. As illustrated in the top panel, glucose levels remained stabilized past day 200 at levels comparable or better than those observed during the period of insulin treatment. The bottom panel confirms that no additional insulin treatments were administered during this time period.

FIG. 10 depicts body weight analysis of canine allotransplantation. The top and bottom panels have been imported from FIG. 9. The middle panel shows the animal body weight monitored during the testing period. As can be seen in this chart, the body weight of the canine remained stable throughout the testing period. FIG. 11 depicts a fructosamine analysis of canine allotransplantation. The top and bottom panels have been imported from FIG. 9. The middle panel shows fructosamine measurements, an indicator of blood glucose level averaged over 2-3 weeks in diabetic subjects. A fructosamine level of 400 is roughly equivalent to an A1C measurement of 8.0, which is a similar indicator. The shaded area in the middle panel shows acceptable fructosamine levels. As can be seen in this chart, the fructosamine level on the tested days falls within the acceptable level. The tested fructosamine level is equivalent to an A1C level ranging from 6.0 (days 110-120) to 8.0 (days 195-200).

Example 6

Repeated Transplantation of Microcapsules in Canines

When fasting hyperglycemia recurs in animal, the transplant procedure of Example 5 may be repeated to maintain normoglycemia. For example, dog 7 received 40,000 EIN/kg, but was only able to maintain some semblance of glucose control for approximately 90 days. The dog was then given a second dosage of encapsulated islets of 63,000 EIN/kg total in two transplants (the transplants were administered a month apart due to the availability of the islets). The normoglycemia lasted approximately 110 days. These results are similar to those observed in the transplantation of dog 6 with 100,000 EIN/kg, and of comparable effectiveness in providing fasting glucose control.

Figure 12:
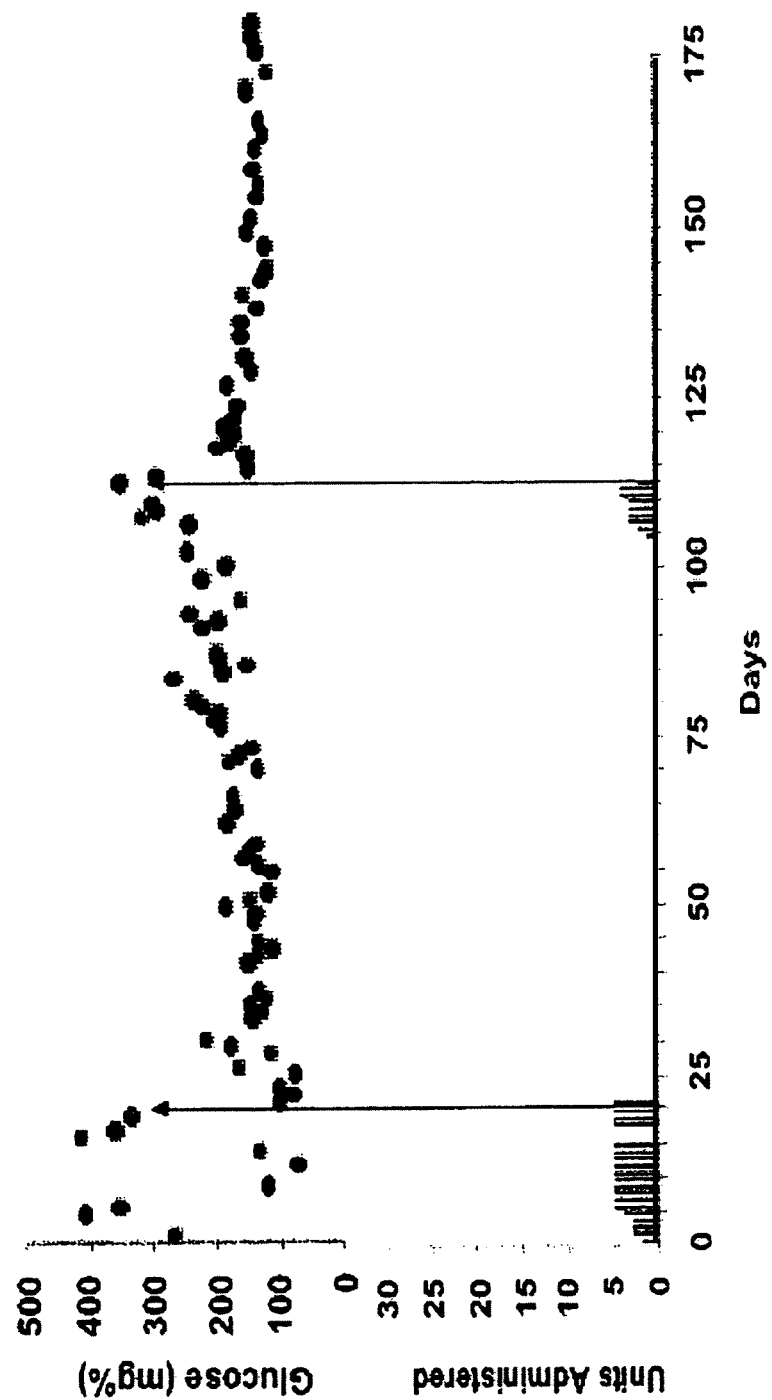
FIG. 12 shows the re-transplantation of encapsulated islets in canine. This chart illustrates an initial allotransplantation and re-transplantation on a canine of islets encapsulated in a multi-membrane system.

FIG. 12 shows the daily fasting blood glucose of dog 7 at 90-110 mg/dl without any supplemental insulin or immunosuppression. The vertical lines show the day of islet transplantation. The top panel shows data points that indicate the venous plasma glucose concentrations collected 12-18 hours following a meal. The lower panel indicates the daily dosage of subcutaneous pork insulin administered, with the upper portion of bar indicating NPH insulin, and the lower portion of bar indicating regular insulin. This figure illustrates the effectiveness of re-transplantation, as evidenced by the glucose levels stabilizing immediately after the second transplantation.

These results suggest additional transplants perform just as well if not better than initial transplantation. It is believed that the subsequent transplant performs better than the initial transplant because of the subject's ability to acclimate to the treatment and minimize vascularization. Re-transplantation provides improved glucose control and was well tolerated in the animal in terms of biocompatibility. Four successful re-transplantations have been performed on one subject; however, there is no practical limit to the number of re-transplantations that can be performed on a subject.

Figure 13:
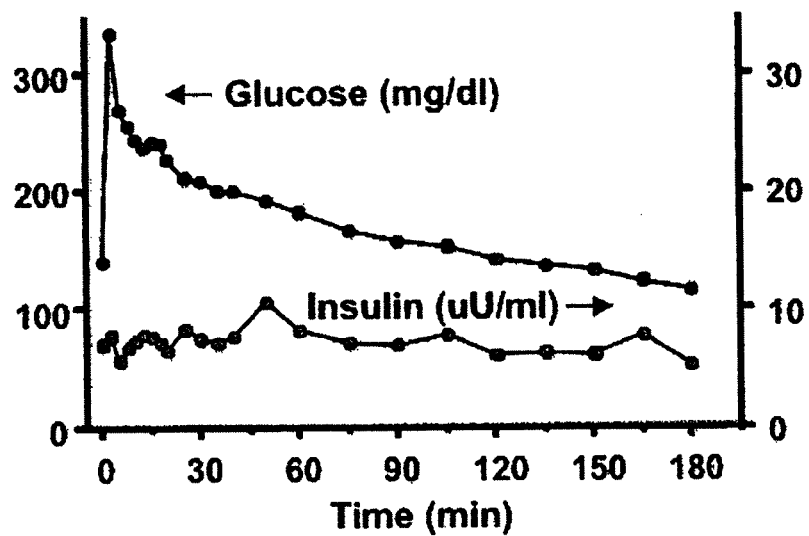
FIG. 13 depicts the results of the Intravenous Glucose Tolerance Test (IVGTT). The chart evaluates intravenous dextrose (300 mg/kg) administration in a canine having previously received a transplantation of islets encapsulated in multi-membrane system.

Intravenous glucose tolerance test (IVGTT) were performed on all animals to assess the in vivo function of encapsulated islets. FIG. 13 illustrates the IVGTT results of dog 5. Intravenous dextrose (300 mg/kg) was administered at t=o in a canine having previously received a transplantation of islets encapsulated in multi-membrane system. Venous samples were collected from the jugular vein to determine plasma glucose and insulin. The subject's blood-glucose level returned to normal at approximately 105 minutes, which is longer, but not unreasonably longer, than the 50-minute average exhibited by 6 control dogs. The rate of glucose clearing (the K value) was high, yet within normal range. Circulating insulin values for all the transplanted animals increased an average of 40% above basal in 75 minutes of the IVGTT and stayed at that level for the remainder of the test. Dogs with encapsulated islets did not demonstrate a first-phase insulin release that is often seen in the control animals. The lack of an insulin spike in response to glucose challenge (likely due to dilution effect of IP transplantation site) may have contributed to the islets gradually losing their ability to secrete sufficient insulin to maintain normoglycemia.

Example 7

Formation of Immunoisolation Patches

Figure 14:
FIG. 14 is a photograph depicting an immunoisolation patch of an embodiment of the present invention, as described in Example 7.
Figure 15:
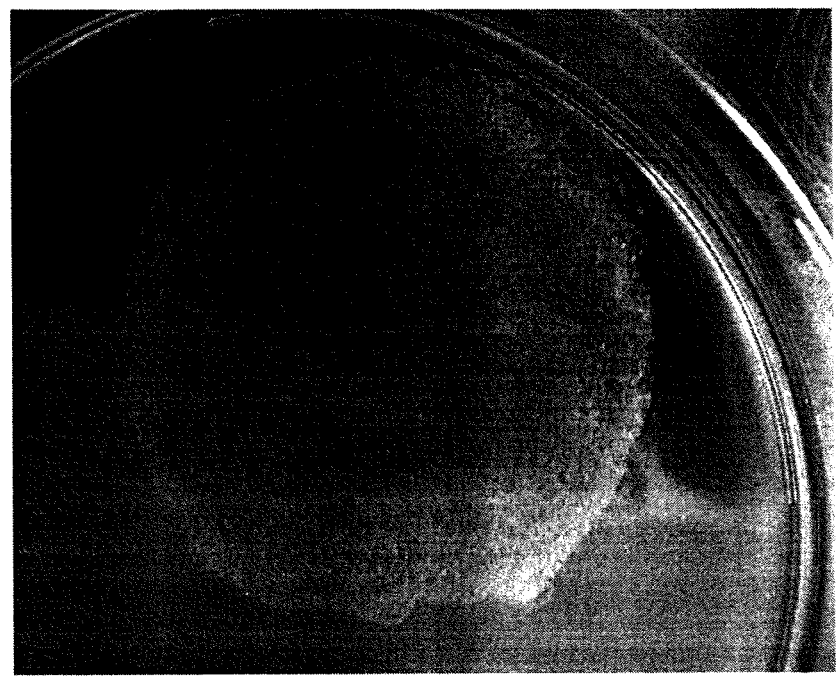
FIG. 15 is a photograph depicting an immunoisolation patch being held up on a vertical surface by surface tension, as described in Example 7.
Figure 16:
FIG. 16 is a photograph illustrating the surgical placement of an immunoisolation patch of an embodiment of the present invention, as described in Example 8.
Figure 17:
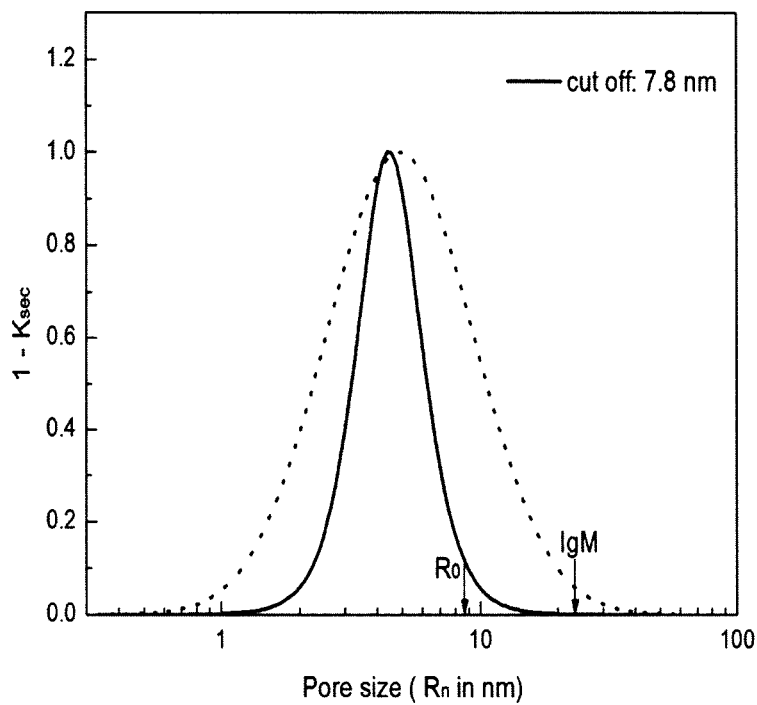
FIG. 17 depicts the pore size distributions of the microcapsule membranes of a microcapsule formed according to an embodiment of the present invention.

Two-membrane microcapsules encapsulating pancreatic islets were prepared as described in Examples 2 and 3, and mixed thoroughly with biocompatible polymers, such as sodium alginate (1.5%-3.0%), at a one-to-one ratio. This mixture was spread onto a non-wetting surface to form a circular patch. A circular non-wetting transparent weight was placed on top of the polymer patch. Gentle FIG. 8 motion of the weight was used to nudge the capsules into a uniform monolayer. With the weight remaining in place, polycation, such as $CaCl_2$, (1%-1.5%), was introduced to the polymer to start the gelling process. As the edge of the patch started to show signs of separation from the surface, the weight was removed to allow the gelling process to continue. In less than 10 minutes, the patches were free-floating and ready to be washed and transferred for storage in an incubator. Various in vitro tests were performed to study the optimal patch parameters, and tradeoffs between mass transport and the mechanical strength of patches. Patches of different pore sizes and mechanical strength were found to be stable and intact after been incubated in a culture medium for 5 weeks at 39 degrees C. FIG. 14 is a photograph depicting an immunoisolation patch prepared in the described manner. This particular patch is circular, approximately 6 cm in diameter, 1 mm in thickness, and contains approximately 6000 microcapsules encapsulating approximately 25,000 pancreatic islets. The microcapsules are formed in a monolayer. FIG. 15 is a photograph demonstrating the ability of an immunoisolation patch to remain in place when in a vertical position in a suspension dish.

Example 8

Canine Immunoisolation Patch Implantation

Immunoisolation patches comprising microcapsules in a biocompatible polymer matrix were formed according to Example 7, and implanted in canines. Healthy male mongrel canines of ~9 kg was utilized as the recipients. The canines underwent a total pancreatectomy 28 days prior to transplantation in order to render the animals totally insulin deficient. 5-7 days prior to islet transplantation, exogenous insulin administration was withheld for 36 hours to verify the success of pancreatectomy. On the day of transplantation, general anesthesia was induced. 3.5-inch midline incisions were performed. A total of twelve microcapsule patches containing 300,000 effective human IEQ were administered on top of the omentum surface, and then the incision was closed. Upon anesthetic recovery ~15 min, animals were provided their daily food ration. No immunosuppressive or anti-inflammatory therapies were utilized. One-month in vivo visual inspection found the microcapsule patches near their original locations with no visible complications.

Data presented in Table 1 below indicates that xenotransplantation was successful, and that there has been continuous improvement of glycemic management. For the first three months, the Lantus® (insulin glargine [rDNA origin] injection, sold by Sanofi Aventis) requirement was reduced by 33%, and average excess blood glucose (BG) level dropped by 33%. Novolin®GE (biosynthetic human insulin, sold by Novo Nordisk) requirement remained steady. The last column of Table 1 showing the average BG level of 85 more than three months after implantation indicates the ability to sustain blood glucose levels over long periods of time.

TABLE 1

| | Pre-Transplant Days | Post-Transplant Days | | | |
|---|---|---|---|---|---|
| | −33 to −1 | 0 to 33 | 34 to 67 | 68 to 101 | 102 to 135 |
| Average Plasma Glucose, mg/dl* | 182 ± 44 | 144 ± 36 | 154 ± 34 | 137 ± 32 | 85 ± 20 |
| Number of Glucose Values ≥ 190 | 6 | 5 | 7 | 4 | 0 |
| Number of Glucose Values ≤ 55 | 2 | 0 | 1 | 0 | 1 |
| Average Daily Novolin ® Adm. | 6 | 6 | 6 | 6 | 6 |
| Average Daily Lantus ® Adm. | 7.4 | 4.9 | 5.3 | 5.1 | 5.6 |

*Mean ± sem

Example 9

Formation of Immunoisolation Patches & In Vitro Testing

Alginate-CS beads laden with islets were introduced into PLL-PMCG bath for membrane formation. Due to its high mobility, PMCG infiltrates Alginate-CS network with ease and forms the inner membrane layer (~30 μm). On the other hand, PLL, due to its low mobility, can only participate with PMCG forming a thin PLL-PMCG/Alginate-CS surface layer (~30 nm). The inner PMCG/Alginate-CS membrane, due to its thickness, plays the key role in mechanical strength and mass transport functions of the capsules. On the other hand, PLL-PMCG/Alginate-CS membrane, due to its uniform pore size distribution, plays the key role in immunoprotection and due to its more stable chemical bonds, the stability. These separations of functions allow more flexibility in the capsule design.

The capsules described above were mixed thoroughly with biocompatible polymers, such as sodium alginate (1.5%-3.0%), at a one-to-one ratio. This mixture was spread onto a non-wetting surface to form a circular patch. A circular non-wetting transparent weight was placed on top of the polymer patch. Gentle FIG. 8 motion of the weight was used to nudge the capsules into a uniform monolayer. With the weight remaining in place, polycation, such as $CaCl_2$, (1%-1.5%), was introduced to the polymer to start the gelling process. As the edge of the patch started to show signs of separation from the surface, the weight was removed to allow the gelling process to continue. In less than 10 minutes, the patches were free-floating and ready to be washed and transferred for storage in an incubator.

An in vitro study was performed to test the stability of the capsule-patch (CP) of different functional parameters and dimensions. Aside from overcoming gravitational sedimentation, lab study has shown planar geometry of CP tolerates better the capsule volume expansion and contraction cycle. Capsules with larger pores (lower polymer density) that collapse in spherical geometry can now be considered, thus, a greater degree of freedom in capsule design. CP of different pore sizes and mechanical strength were found to be stable and intact after being incubated in different culture mediums for 5 weeks at 39° C.

Example 10

Additional Studies in Canines

Figure 18:
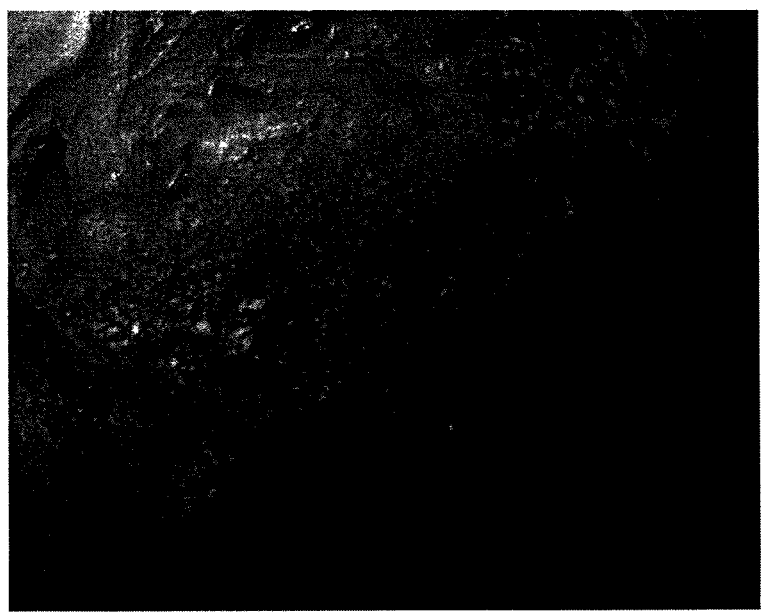
FIG. 18 is a photograph depicting an immunoisolation patch retrieved from a canine host five months after initial transplantation in subcutaneous space, as described in Example 10.

Capsules and immunoisolation patches were formed according to Example 9. A study was performed to test the effectiveness of the immunoisolation patches in the subcutaneous space in order to enhance a stratified engraftment of encapsulated islets to maximize the encapsulated islet environment. A pancreatectomized canine weighing ~6 kg was utilized as the recipient. A capsule-patch containing 25,000 canine IEQ was transplanted into the subcutaneous space on the side of the animal. Postmortem examination at five months revealed encapsulated islets were in the original location and embedded into the subcutaneous layer. The capsules were visibly intact with some neovascularization on the dorsal surface of the embedded encapsulated islets, as depicted in FIG. 18 (depicting a capsule-patch retrieved from canine number 626).

Figure 19:
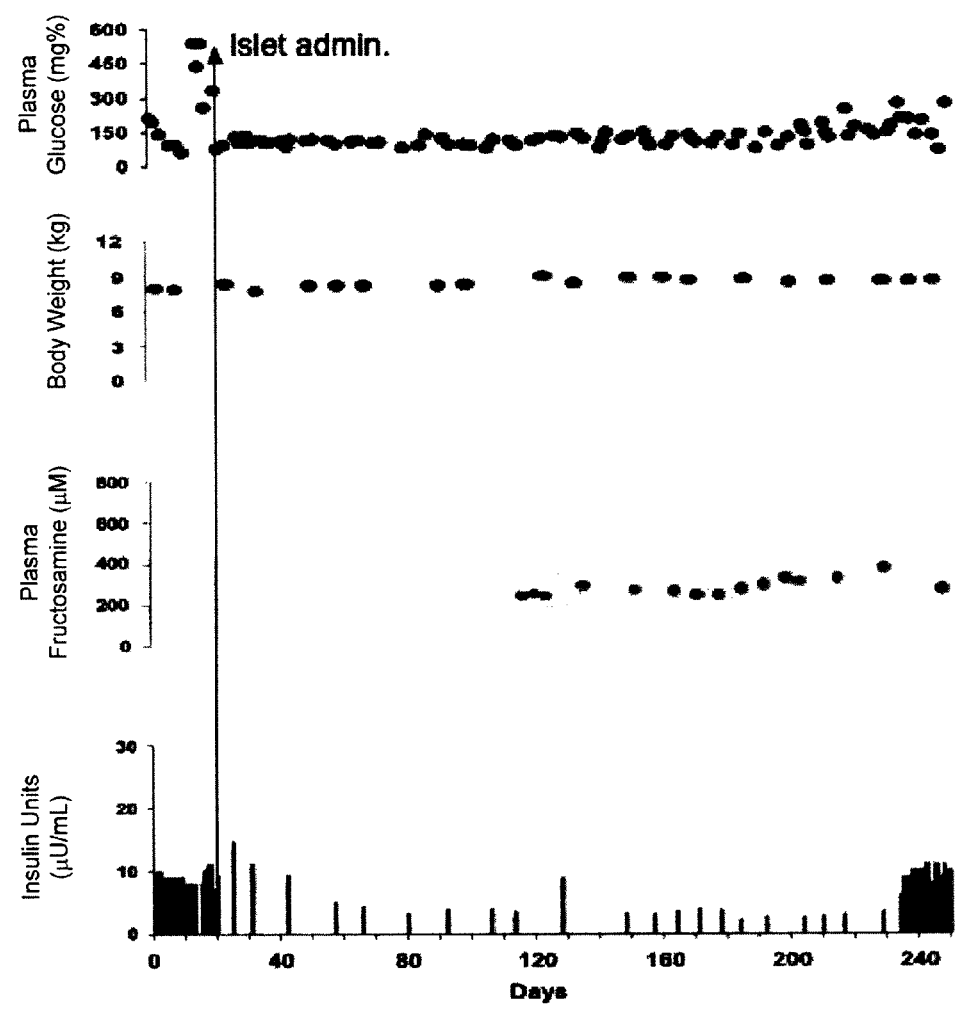
FIG. 19 depicts blood glucose, fructosamine and insulin analysis, as well as body weight analysis, of a canine having an implanted immunoisolation patch, as described in Example 10.

In another study, the capsules were transplanted into nine totally pancreatectomized dogs, and normalized fasting blood glucose levels in nine out of nine dogs for up to two-hundred and fourteen days with a single transplantation. Fasting glucose concentrations, body weight, plasma fructosamine measurements and insulin levels (exogenous and endogenous) of canine number 141 are shown in FIG. 19 as representative data. Re-transplantation was assessed in three animals, and encapsulated islets were effective in providing fasting glycolic control after the initial transplantation had run its course. No immunosuppressant or anti-inflammatory therapy was utilized.

In FIG. 19, the upper panel indicates venous plasma glucose concentrations collected 6-18 hours following a meal, the second panel from the top indicates the recipient's body weight in kilograms, the third panel from the top indicates venous plasma fructosamine concentrations, and the bottom panel indicates insulin levels. Insulin levels include levels of exogenous insulin (NPH or regular pork insulin), which was administered daily up until the time of islet administration, and then again after 214 days, and levels of circulating endogenous insulin, which was measured as the circulating plasma insulin concentration (fasting) assessed at the same time that the daily glucose measurements were performed.

A study was also performed to test the ability of the immunoisolation patch (capsule-patch) to anchor encapsulated islets on the omental surface, and its effectiveness in providing xenoprotection of human islets in the canine model. Totally pancreatectomized male mongrel canines of ~9 kg were utilized as the recipients. Capsule-patches containing less than one-third of the needed dosage of human IEQ for insulin independence were administered on top of the omental surface. No immunosuppressive or anti-inflammatory therapies were utilized. One-month in vivo visual inspection found the capsule-patches (CP) near their original locations with no visible complications. Post-mortem examination (>5 months) showed that almost all the capsules stayed on the omental surface. The majority of them were intact with viable islets. The transplantation of sub-dosage encapsulated islets offered therapeutic benefits as seen in Table 2. This experiment demonstrated the effectiveness of CP overcoming the gravitational sedimentation problem as well as providing excellent immunoprotection.

TABLE 2

| | Pre-Transplant Days | Post-Transplant Days | | | |
|---|---|---|---|---|---|
| | −33 to −1 | 0 to 33 | 34 to 67 | 68 to 101 | 102 to 120 |
| Average Plasma Glucose, mg/dl* | 182 ± 44 | 144 ± 36 | 154 ± 34 | 137 ± 32 | 81 ± 25 |
| Number of Glucose Values ≥ 190 | 6 | 5 | 7 | 4 | 0 |
| Number of Glucose Values ≤ 55 | 2 | 0 | 1 | 0 | 1 |
| Average Daily Lantus ® Adm. | 7.4 | 4.9 | 5.3 | 5.1 | 5.6 |

*Mean ± sem

The above description, drawings and examples are only illustrative of preferred embodiments which achieve the objects, features and advantages of the present invention. It is not intended that the present invention be limited to the illustrative embodiments. Any modification of the present invention which comes within the spirit and scope of the following claims should be considered part of the present invention.

What is claimed is:

1. An immunoisolation patch for use in cellular transplantation therapy of a disorder, comprising:
   a plurality of multi-membrane microcapsules which encapsulate cellular material; and
   a biocompatible support matrix in which the plurality of multi-membrane microcapsules are distributed;
   wherein at least some of said plurality of multi-membrane microcapsules comprise at least two membrane layers:
      an inner membrane biocompatible with the encapsulated cellular material, the inner membrane comprising sodium alginate, cellulose sulfate, and a multi-component polycation; and
      an outer membrane which provides chemical stability to the immunoisolation patch and which bonds the microcapsule to the support matrix, the outer membrane comprising a polyion and at least one compound selected from the group consisting of sodium alginate, cellulose sulfate, and poly(methylene-co-guanidine); and
   wherein the support matrix comprises a carbohydrate polymer having carboxylate or sulfate groups, and an inorganic salt.

2. The immunoisolation patch of claim 1, wherein the disorder is an endocrine disorder.

3. The immunoisolation patch of claim 2, wherein the endocrine disorder is diabetes and the cellular material is pancreatic beta cells, pancreatic islets, or other insulin-producing islets, or a combination thereof.

4. The immunoisolation patch of claim 2, wherein the endocrine disorder is hypothyroidism and the cellular material comprises one or more of thyroid follicular cells, parafollicular cells, or thyroid follicles.

5. The immunoisolation patch of claim 1, wherein the disorder is a neurological disorder.

6. An immunoisolation patch for use in cellular transplantation therapy for a pancreatic disorder, comprising:
a plurality of multi-membrane microcapsules which encapsulate pancreatic cellular material; and
a biocompatible support matrix in which the plurality of multi-membrane microcapsules are distributed;
wherein at least some of said plurality of multi-membrane microcapsules comprise at least two membrane layers:
an inner membrane biocompatible with the encapsulated cellular material, the inner membrane comprising sodium alginate, cellulose sulfate, and a multi-component polycation; and
an outer membrane which provides chemical stability to the immunoisolation patch and which bonds the microcapsule to the support matrix, the outer membrane comprising a polyion and at least one compound selected from the group consisting of sodium alginate, cellulose sulfate, and poly(methylene-co-guanidine); and
wherein the support matrix comprises a carbohydrate polymer having carboxylate or sulfate groups, and an inorganic salt.

7. The immunoisolation patch of claim 6, wherein the pancreatic disorder is diabetes and the pancreatic cellular material is pancreatic beta cells, pancreatic islets, or other insulin-producing islets, or a combination thereof.

8. The immunoisolation patch of claim 7, wherein the pancreatic cellular material is pancreatic islets.

9. The immunoisolation patch of claim 1, wherein:
the inner membrane is about 5 to about 100 microns thick, and the outer membrane is less than about 5 microns thick, and
the multi-membrane microcapsule has a porosity cutoff of about 50 to about 250 kilodaltons.

10. The immunoisolation patch of claim 1, wherein the multi-component polycation of the inner membrane comprises polymethylene-co-guanidine and one or both of calcium chloride and sodium chloride and wherein the polyion of the outer membrane is selected from the group consisting of poly-L-lysine, poly-D-lysine, poly-L,D-lysine, poly-L-ornithine, poly-D-ornithine, poly-L,D-ornithine, chitosan, polyacrylamide, poly(vinyl alcohol), and combinations thereof.

11. The immunoisolation patch of claim 1, wherein the inner membrane comprises calcium chloride, cellulose sulfate, polymethylene-co-guanidine and sodium alginate, the outer membrane comprises cellulose sulfate, poly-L-lysine, polymethylene-co-guanidine, and sodium alginate, and the support matrix comprises calcium chloride and sodium alginate.

12. The immunoisolation patch of claim 1, wherein each of the membranes comprises at least one compound selected from the group consisting of calcium chloride, cellulose sulfate, poly-L-lysine, polymethylene-co-guanidine and sodium alginate and wherein the plurality of multi-membrane microcapsules are distributed in the support matrix as a monolayer.

13. A method of cellular transplantation therapy of a disorder, comprising:
administering to a mammalian subject in need thereof an immunoisolation patch, wherein the immunoisolation patch comprises:
a plurality of multi-membrane microcapsules which encapsulate cellular material; and
a biocompatible support matrix in which the plurality of multi-membrane microcapsules are distributed,
wherein at least some of said plurality of multi-membrane microcapsules comprise at least two membrane layers:
an inner membrane biocompatible with the encapsulated cellular material, the inner membrane comprising sodium alginate, cellulose sulfate, and a multi-component polycation; and
an outer membrane which provides chemical stability to the immunoisolation patch and which bonds the microcapsule to the support matrix, the outer membrane comprising a polyion and at least one compound selected from the group consisting of sodium alginate, cellulose sulfate, and poly(methylene-co-guanidine), and
wherein the support matrix comprises a carbohydrate polymer having carboxylate or sulfate groups, and an inorganic salt.

14. The method of claim 13, wherein the disorder is selected from diabetes, hypothyroidism, and a neurological disorder.

15. The method of claim 13, wherein:
the inner membrane is about 5 to about 100 microns thick and the outer membrane is less than about 5 microns thick, and
the multi-membrane microcapsule has a porosity cutoff of about 50 to about 250 kilodaltons.

16. The method of claim 13, wherein:
the multi-component polycation of the inner membrane comprises polymethylene-co-guanidine and one or both of calcium chloride and sodium chloride, and the polyion of the outer membrane is selected from the group consisting of poly-L-lysine, poly-D-lysine, poly-L,D-lysine, poly-L-ornithine, poly-D-ornithine, poly-L,D-ornithine, chitosan, polyacrylamide, poly(vinyl alcohol), and combinations thereof.

17. The method of claim 13, wherein:
the inner membrane comprises calcium chloride, cellulose sulfate, polymethylene-co-guanidine and sodium alginate,
the outer membrane comprises cellulose sulfate, poly-L-lysine, polymethylene-co-guanidine, and sodium alginate, and
the support matrix comprises calcium chloride and sodium alginate.

18. The method of claim 13, wherein each of the membranes and the support matrix comprises at least one compound selected from the group consisting of calcium chloride, cellulose sulfate, poly-L-lysine, polymethylene-co-guanidine and sodium alginate and the plurality of multi-membrane microcapsules are distributed in the support matrix as a monolayer.

19. A method of cellular transplantation therapy of a pancreatic disorder, comprising:
administering to a mammalian subject in need thereof an immunoisolation patch, wherein the immunoisolation patch comprises:
a plurality of multi-membrane microcapsules which encapsulate pancreatic cellular material; and a biocompatible support matrix in which the plurality of multi-membrane microcapsules are distributed, wherein at least some of said plurality of multi-membrane microcapsules comprise at least two membrane layers:

an inner membrane biocompatible with the encapsulated cellular material, the inner membrane comprising sodium alginate, cellulose sulfate, and a multi-component polycation; and an outer membrane which provides chemical stability to the immunoisolation patch and which bonds the microcapsule to the support matrix, the outer membrane comprising a polyion and at least one compound selected from the group consisting of sodium alginate, cellulose sulfate, and poly(methylene-co-guanidine), and wherein the support matrix comprises a carbohydrate polymer having carboxylate or sulfate groups, and an inorganic salt.

20. The method of claim 19, wherein the pancreatic disorder is diabetes and the pancreatic cellular material is pancreatic beta cells, pancreatic islets, or other insulin-producing islets, or a combination thereof.

21. A method of stabilizing the glucose level in a mammalian subject for at least 30 days, comprising:

administering to a mammalian subject in need thereof an immunoisolation patch, wherein the immunoisolation patch comprises:

a plurality of multi-membrane microcapsules which encapsulate pancreatic cellular material; and a biocompatible support matrix in which the plurality of multi-membrane microcapsules are distributed, wherein at least some of said plurality of multi-membrane microcapsules comprise at least two membrane layers:

an inner membrane biocompatible with the encapsulated cellular material, the inner membrane comprising sodium alginate, cellulose sulfate, and a multi-component polycation; and an outer membrane which provides chemical stability to the immunoisolation patch and which bonds the microcapsule to the support matrix, the outer membrane comprising a polyion and at least one compound selected from the group consisting of sodium alginate, cellulose sulfate, and poly(methylene-co-guanidine), and wherein the support matrix comprises a carbohydrate polymer having carboxylate or sulfate groups, and an inorganic salt;

wherein said administration results in a stabilization of the glucose level in the mammalian subject for at least 30 days.

22. The method of claim 21, wherein the subject is a human.

* * * * *